US010682401B2

(12) United States Patent
Lawman et al.

(10) Patent No.: US 10,682,401 B2
(45) Date of Patent: *Jun. 16, 2020

(54) MULTI-INDICATION MRNA CANCER IMMUNOTHERAPY

(71) Applicant: MORPHOGENESIS, INC., Tampa, FL (US)

(72) Inventors: Michael J. P. Lawman, Temple Terrace, FL (US); Patricia D. Lawman, Temple Terrace, FL (US); Meghan Gentilini, Tampa, FL (US); Vijay Ramiya, Tampa, FL (US); Marina Victor Abdelmaseeh Bastawrous, Port Orange, FL (US); Michael J. Shamblott, St. Petersburg, FL (US)

(73) Assignee: MORPHOGENESIS, INC., Tampa, FL (US)

( * ) Notice: Subject to any disclaimer, the term of this patent is extended or adjusted under 35 U.S.C. 154(b) by 209 days.

This patent is subject to a terminal disclaimer.

(21) Appl. No.: 15/583,599

(22) Filed: May 1, 2017

(65) Prior Publication Data

US 2017/0232090 A1    Aug. 17, 2017

Related U.S. Application Data

(63) Continuation of application No. 15/114,943, filed as application No. PCT/US2016/033235 on May 19, 2016, now Pat. No. 9,636,388.

(60) Provisional application No. 62/163,446, filed on May 19, 2015.

(51) Int. Cl.
| | |
|---|---|
| *C07H 21/04* | (2006.01) |
| *A61K 31/70* | (2006.01) |
| *A61K 48/00* | (2006.01) |
| *A61K 39/00* | (2006.01) |
| *A61K 45/06* | (2006.01) |
| *A61K 39/09* | (2006.01) |
| *A01K 67/00* | (2006.01) |

(52) U.S. Cl.
CPC ........ *A61K 39/0011* (2013.01); *A61K 39/092* (2013.01); *A61K 45/06* (2013.01); *A61K 2039/5152* (2013.01); *A61K 2039/5156* (2013.01); *A61K 2039/5256* (2013.01); *A61K 2039/53* (2013.01); *A61K 2039/54* (2013.01); *A61K 2039/552* (2013.01); *A61K 2039/575* (2013.01); *A61K 2039/585* (2013.01)

(58) Field of Classification Search
CPC .. A61K 39/0011; A61K 45/06; A61K 39/092; A61K 2039/54; A61K 2039/53; A61K 2039/5152; A61K 2039/5156
See application file for complete search history.

(56) References Cited

U.S. PATENT DOCUMENTS

| | | |
|---|---|---|
| 7,094,603 B2 | 8/2006 | Lawman et al. |
| 7,348,015 B2 | 3/2008 | Lawman et al. |
| 7,795,020 B2 | 9/2010 | Lawman et al. |
| 8,680,069 B2 | 3/2014 | de Fougerolles et al. |
| 9,636,388 B2 | 5/2017 | Lawman et al. |
| 2002/0141981 A1 | 10/2002 | Lawman et al. |
| 2005/0106130 A1 | 5/2005 | Lawman et al. |
| 2008/0166379 A1 | 7/2008 | Lawman et al. |
| 2008/0311155 A1 | 12/2008 | Nicolette et al. |
| 2016/0361400 A1 | 12/2016 | Lawman et al. |
| 2016/0367651 A1 | 12/2016 | Shiku et al. |

FOREIGN PATENT DOCUMENTS

| | | |
|---|---|---|
| JP | 2008-513009 | 5/2008 |
| WO | WO 99/36433 | 7/1999 |
| WO | WO 2009/117011 | 9/2009 |
| WO | WO 2015/050158 | 4/2015 |
| WO | WO 2015/134577 | 9/2015 |

OTHER PUBLICATIONS

Kay et al. Molecular cloning of cDNA sequences coding for the major alpha- and beta-globin polypeptides of adult Xenopus laevis. Nucleic Acids Research 8:2691-2707, (Year: 1980).*
Kruys et al. The 3' untranslated region of the human interferon-beta mRNA has an inhibitory effect on translation. Proc. Natl. Acad. Sci. USA 84:6030-6034, (Year: 1987).*
Bringmann, A. et al. "RNA Vaccines in Cancer Treatment" *Journal of Biomedicine and Biotechnology*, 2010, pp. 1-13, vol. 2010, Article ID 623687.
Fotin-Mleczek, M. et al. "Highly potent mRNA based cancer vaccines represent an attractive platform for combination therapies supporting an improved therapeutic effect" *The Journal of Gene Medicine*, 2012, pp. 428-439, vol. 14.
Geall, A.J. et al. "RNA: The new revolution in nucleic acid vaccines" *Seminars in Immunology*, 2013, pp. 152-159, vol. 25, No. 2.
Kreiter, S. et al. "Tumor vaccination using messenger RNA: prospects of a future therapy" *Current Opinion in Immunology*, 2011, pp. 399-406, vol. 23, No. 3.
Leitner, W.W. et al. "DNA and RNA-based vaccines: principles, progress and prospects" *Vaccine*, Dec. 10, 1999, pp. 765-777, vol. 18, No. 9-10.
McNamara, M.A. et al. "RNA-Based Vaccines in Cancer Immunotherapy" *Journal of Immunology Research*, 2015, pp. 1-9, vol. 2015, Article ID 794528.

(Continued)

*Primary Examiner* — Quang Nguyen
(74) *Attorney, Agent, or Firm* — Saliwanchik, Lloyd & Eisenschenk

(57) ABSTRACT

Synthetic bacterial messenger RNA can be used to prepare autologous, allogenic or direct nucleic acid cancer vaccines. Cancer cells are transfected either in vitro or in vivo with mRNA obtained from DNA that encodes an immunogenic bacterial protein. An immune response to the cancer is generated from direct administration of the mRNA in vivo or administration of vaccines prepared from cancer cells in vitro.

8 Claims, 10 Drawing Sheets

Specification includes a Sequence Listing.

(56) References Cited

OTHER PUBLICATIONS

Pollard, C. et al. "Challenges and advances toward the rational design of mRNA vaccines" *Trends in Molecular Medicine*, 2013, pp. 1-9, vol. 19, No. 12.

Sahin, U. et al. "mRNA-based therapeutics—developing a new class of drugs" *Nature Reviews Drug Discovery*, 2014, pp. 759-780, vol. 13, No. 10.

Schlake, T. et al. "Developing mRNA-vaccine technologies" *RNA Biology*, Nov. 2012, pp. 1319-1330, vol. 9, No. 11.

Shedlock, D.J. et al. "DNA vaccination: antigen presentation and the induction of immunity" *Journal of Leukocyte Biology*, Dec. 2000, pp. 793-806, vol. 68.

Tavernier, G. et al. "mRNA as gene therapeutic: How to control protein expression" *Journal of Controlled Release*, 2011, pp. 238-247, vol. 150, No. 3.

Van Lint, S. et al. "mRNA: From a chemical blueprint production to an off-the shelf therapeutic" *Human Vaccines & Immunotherapeutics*, Feb. 2013, pp. 265-274, vol. 9, No. 2.

Carralot, J-P. et al. "Production and characterization of amplified tumor-derived cRNA libraries to be used as vaccines against metastatic melanomas" *Genetic Vaccines and Therapy*, Aug. 22, 2005, pp. 1-10, vol. 3, No. 6.

Chamas, F. et al. "Role of the 5' untranslated region (UTR) in the tissue-specific regulation of rat tryptophan hydroxylase gene expression by stress" *Journal of Neurochemistry*, 2002, pp. 645-654, vol. 82, No. 3.

Chetverin, A. B. "Replicable and recombinogenic RNAs" *FEBS Letters*, 2004, pp. 35-41, vol. 567, No. 1.

Cleaver, O. B. et al. "Overexpression of the tinman-related genes XNkx-2.5 and XNkx-2.3 in Xenopus embryos results in myocardial hyperplasia" *Development*, 1996, pp. 3549-3556, vol. 122, No. 11.

Conry, R. M. et al. "Characterization of a Messenger RNA Polynucleotide Vaccine Vector" *Cancer Research*, Apr. 1, 1995, pp. 1397-1400, vol. 55, No. 7.

Fotin-Mleczek, M. et al. "Highly potent mRNA based cancer vaccines represent an attractive platform for combination therapies supporting an improved therapeutic effect" *The Journal of Gene Medicine*, 2012, pp. 428-439, vol. 14, No. 6.

Geall, A. J. et al. "Nonviral delivery of self-amplifying RNA vaccines" *Proceedings of the National Academy of Sciences of the United States of America*, Sep. 4, 2012, pp. 14604-14609, vol. 109, No. 36.

Hoerr, I. et al. "In vivo application of RNA leads to induction of specific cytotoxic T lymphocytes and antibodies" *European Journal of Immunology*, 2000, pp. 1-7, vol. 30, No. 1.

Kreiter, S. et al. "Increased Antigen Presentation Efficiency by Coupling Antigens to MHC Class I Trafficking Signals" *The Journal of Immunology*, 2008, pp. 309-318, vol. 180, No. 1, Corrections, p. 319.

Kreiter, S. et al. "Intranodal Vaccination with Naked Antigen-Encoding RNA Elicits Potent Prophylactic and Therapeutic Antitumoral Immunity" *Cancer Research*, Nov. 15, 2010, pp. 9031-9040, vol. 70, No. 22.

Krieg, P. A. et al. "Functional messenger RNAs are produced by SP6 in vitro transcription of cloned cDNAs" *Nucleic Acids Research*, 1984, pp. 7057-7070, vol. 12, No. 18.

Kuhn, A. N. et al. "Phosphorothioate cap analogs increase stability and translational efficiency of RNA vaccines in immature dendritic cells and induce superior immune responses in vivo" *Gene Therapy*, Apr. 22, 2010, pp. 961-971, vol. 17, No. 8.

Malone, R. W. et al. "Cationic liposome-mediated RNA transfection" *Procedures of National Academy of Sciences of the United States of America*, Aug. 1989, pp. 6077-6081, vol. 86, No. 16.

Noderer, W. L. et al. "Quantitative analysis of mammalian translation initiation sites by FACS-seq" *Molecular Systems Biology*, 2014, pp. 1-14, vol. 10.

Probst, J. et al. "Spontaneous cellular uptake of exogenous messenger RNA in vivo is nucleic acid-specific, saturable and ion dependent" *Gene Therapy*, 2007, pp. 1175-1180, vol. 14, No. 15.

Wang, Z. et al. "An mRNA Stability Complex Functions with Poly(A)-Binding Protein To Stabilize mRNA In Vitro" *Molecular and Cellular Biology*, Jul. 1999, pp. 4552-4560, vol. 19, No. 7.

Zhao, Y. et al. "Multiple injections of electroporated autologous T cells expressing a chimeric antigen receptor mediate regression of human disseminated tumor" *Cancer Research*, Nov. 15, 2010, pp. 9053-9061, vol. 70, No. 22.

Pascolo, S. "Vaccination With Messenger RNA" *Methods in Molecular Medicine*, 2006, pp. 23-40, vol. 127.

Fotin-Mleczek, M. et al. "Messenger RNA-based Vaccines With Dual Activity Induce Balanced TLR-7 Dependent Adaptive Immune Responses and Provide Antitumor Activity" *Journal of Immunotherapy*, Jan. 2011, pp. 1-15, vol. 34, No. 1.

Yamamoto, A. et al. "Current Prospects for mRNA gene delivery" *European Journal of Pharmaceutics and Biopharmaceutics*, 2009, pp. 484-489, vol. 71, No. 3.

Wolff, J. A. et al. "Direct Gene Transfer into Mouse Muscle in Vivo" *Science*, Mar. 23, 1990, pp. 1465-1468, vol. 247.

Wilkie, G. S. et al. "Regulation of mRNA translation by 5'- and 3'-UTR-binding factors" *Trends in Biochemical Sciences*, Apr. 2003, pp. 182-188, vol. 28, No. 4.

Kormann, M. S. D., et al. "Expression of therapeutic proteins after delivery of chemically modified mRNA in mice" *Nature Biotechnology*, Feb. 2011, pp. 154-159, vol. 29, No. 2.

Zhou, W. Z. et al. "RNA Melanoma Vaccine: Induction of Antitumor Immunity by Human Glycoprotein 100 mRNA Immunization" *Human Gene Therapy*, Nov. 1, 1999, pp. 2719-2724, vol. 10.

Bialkowski, L. et al. "Intralymphatic mRNA vaccine induces CD8 T-cell responses that inhibit the growth of mucosally located tumours" *Scientific Reports*, Mar. 2, 2016, pp. 1-15, vol. 6, Article No. 22509.

Orlandini Von Niessen, A. G. et al. "Improving mRNA-Based Therapeutic Gene Delivery by Expression-Augmenting 3' UTRs Identified by Cellular Library Screening" *Molecular Therapy*, Apr. 2019, pp. 824-836, vol. 27, No. 4.

Pastor, F. et al. "An RNA toolbox for cancer immunotherapy" *Nature Reviews Drug Discovery*, Sep. 7, 2018, pp. 751-767, vol. 17, No. 100.

Boyle, M. D.P. et al. "Characterization of a Gene Coding for a Type IIo Bacterial IgG-Binding Protein" *Molecular Immunology*, 1995, pp. 669-678, vol. 32, No. 9.

Lawman, M. et al. "Anti-tumor response induced by autologous cancer vaccine in canine lymphoma" *Cancer Therapy*, 2008, pp. 827-840, vol. 6.

\* cited by examiner

| Published clinical trials on tumor vaccination using mRNA. | | | | | |
|---|---|---|---|---|---|
| | Cancer type | Antigen/route | Number of patients | Immune response | Clinical response |
| 2011, Kreiter et al. | Acute myeloid leukemia | WT1 mRNA/i.d. | 10 | CD8$^+$ T-cell responses against multiple WT1 epitopes were detected | 3/10 CR |
| mRNA-based DC vaccination | | | | | |
| 2010, Van Tendeloo et al. [56] | Acute myeloid leukemia | WT1 mRNA/i.d. | 10 | CD8$^+$ T-cell responses against multiple WT1 epitopes were detected | 3/10 CR |
| 2007, Kyte et al. [55] | Metastatic melanoma | Autologous total tumor mRNA/i.d. | 2 | Broad spectrum of CD8$^+$ and CD4$^+$ T-cell responses against tumor antigens | 2 PD |
| 2006, Kyte et al. [11] | Metastatic melanoma | Autologous total tumor mRNA/i.d.-i.n. | 22 | 9/19 patients had measurable T-cell responses, response rate was not higher in the i.n. group | 2/20 SD, 18/20 PD |
| 2005, Mu et al. [54] | Prostate cancer | mRNA from prostate cancer cell lines/i.d.-i.n. | 20 | 12/19 patients developed a specific immune response (8/9 i.d., 4/10 i.n.), decrease in log-slope PSA in 13/19 patients | 11/19 SD |
| 2005, Dannull et al. [53] | Renal cell carcinoma/ovarian carcinoma | Autologous total tumor mRNA +/- Treg depletion/i.d. | 11 | 10/11 patients had T-cell responses, 16 fold increased tumor specific T cell frequencies in patients receiving combined treatment | 8/11 PD |
| 2005, Su et al. [10] | Prostate cancer | Chimeric hTERT-LAMP-1 mRNA/i.d. | 20 | 19/20 patients developed T-cell responses, patients receiving DCs transfected with a chimeric telomerase mRNA developed higher frequencies of CD4$^+$ T cells | Short term decrease in log-slope PSA, transient elimination of CTCs in 5/6 patients, no PR |

FIG. 3

| Published clinical trials on tumor vaccination using mRNA. | | | | |
|---|---|---|---|---|
| 2011, Kreiter, et al. | Cancer type | Antigen/route | Number of patients | Immune response | Clinical response |
| mRNA-based DC vaccination | | | | | |
| 2005, Caruso et al. [52] | Neuroblastoma | Autologous total tumor mRNA/i.d.-i.v. | 11 | 2/11 increase in antitumor antibodies | 1 SD 14 months after diagnosis, 10 PD |
| 2004, Caruso et al. [51] | Brain cancer | Autologous total tumor mRNA/i.d.-i.v. | 9 | 2/7 patients showed a tumor-specific immune response | 2/7 SD, 1/7 PR, 4/7 PD |
| 2003, Morse et al. [50] | Lung, breast, colon cancer | CEA mRNA/i.d. | 42 | Tumor specific T-cell responses were observed | 1/24 CR, 3/24 SD, 18/24 PD, 2/24 MR |
| 2003, Su et al. [9] | Renal cell carcinoma | Autologous total tumor mRNA/i.d./i.v. | 15 | 6/7 patients showed T-cell responses against tumor-antigens | Clinical response was not reliably assessed as patients also underwent other therapies |
| 2002, Heiser et al. [8] | Prostate cancer | PSA mRNA/i.d.-i.v. | 13 | PSA-specific T-cell responses were detected in all patients | Significant decrease in log-slope PSA in 6/7 patients, transient elimination of CTCs in 3 patients |
| Direct vaccination with mRNA | | | | | |
| 2010, Rittig et al. [19] | Renal cell carcinoma | (MUC1, CEA, Her-2/neu, telomerase, survivin, MAGE-A1 mRNA) + GM-CSF/i.d. | 30 | $CD8^+$ (8/10) and $CD4^+$ (4/8) T-cell responses against multiple antigens | 1/30 PR, 15/30 SD, 14/30 PD |

FIG. 3 (continued)

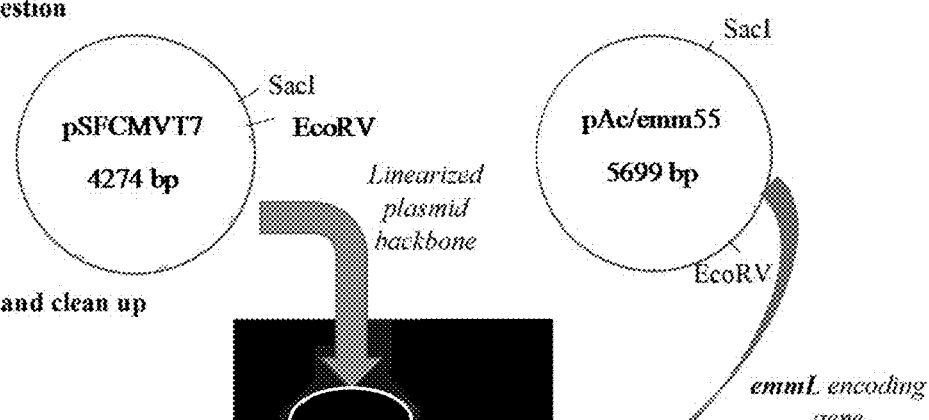
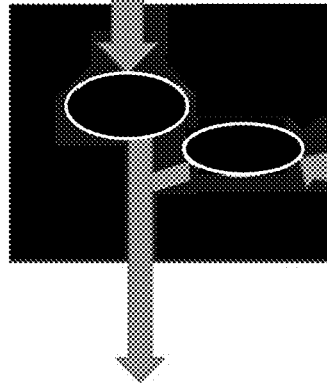
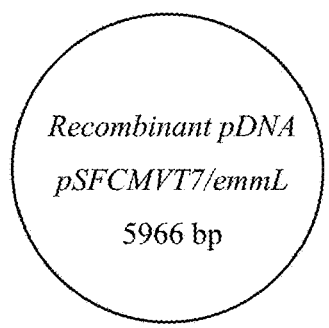
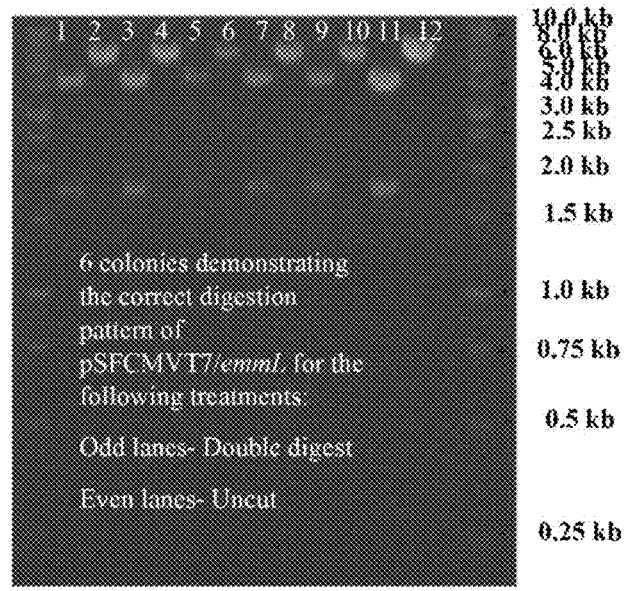
FIG. 5 mRNA 5+ times better expression than DNA

| | Flu. | Ph. | Percent Flu. | |
|---|---|---|---|---|
| DNA 5 µg | | | | 4.17% |
| 1 | 2 | 57 | 3.51% | |
| 2 | 1 | 32 | 3.13% | |
| 3 | 4 | 68 | 5.88% | |
| DNA 20 µg | | | | 8.96% |
| 1 | 2 | 27 | 7.41% | |
| 2 | 7 | 58 | 12.07% | |
| 3 | 2 | 27 | 7.41% | |
| RNA 5 µg | | | | 21.09% |
| 1 | 2 | 11 | 18.18% | |
| 2 | 10 | 48 | 20.83% | |
| 3 | 8 | 33 | 24.24% | |
| RNA 20 µg | | | | 73.78% |
| 1 | 21 | 37 | 56.76% | |
| 2 | 64 | 73 | 87.67% | |
| 3 | 40 | 52 | 76.92% | |

10 million cells, 0.4 cuvette, 300 µL Mirus buffer, 260 Volts and 750 µF

MULTI-INDICATION MRNA CANCER IMMUNOTHERAPY

CROSS-REFERENCE TO RELATED APPLICATIONS

This application is a continuation-in-part of U.S. application Ser. No. 15/114,943, filed Jul. 28, 2016, now U.S. Pat. No. 9,636,388, which is the U.S. national stage application of International Patent Application No. PCT/US2016/033235, filed May 19, 2016, which claims the benefit of U.S. Provisional Application Ser. No. 62/163,446, filed May 19, 2015, the disclosures of which are hereby incorporated by reference in their entirety, including all figures, tables and amino acid and nucleic acid sequences.

The Sequence Listing for this application is labeled "Seq-List.txt" which was created on May 1, 2017 and is 24 KB. The entire content of the sequence listing is incorporated herein by reference in its entirety.

BACKGROUND OF THE INVENTION

1. Field of the Invention

The invention relates generally to vaccines and particularly to cancer vaccines prepared by either transfection of cancer cells or direct intratumoral administration with a synthetic bacterial messenger ribonucleic acid (mRNA).

The present invention provides for development and use of effective mRNA vaccines for cancer treatment. While deoxyribonucleic acid (DNA) vaccines have several deficiencies, including low transfection efficiency and time consuming delivery methods, the mRNA vaccines of the present invention are administered directly into tumor cells and immediately translated into an immunogenic protein which evokes a multi-tumor-antigen response. The short in vivo half-life of mRNA makes it less likely to integrate into the host genome compared to plasmid DNA and is therefore considered safer. Unlike DNA, mRNA-vaccines do not need to cross the nuclear envelope and thus can often generate more rapid and higher levels of protein expression. Additionally, expression of transfected mRNA is cell cycle independent and since the level of mRNA is not driven by a promoter, protein expression and vaccine dosage can be modulated by changing the level of mRNA transfected. In contrast to peptides, mRNA vaccines lack Major Histocompatibility Complex (MHC) haplotype restriction and can be designed to be self-adjuvating with the addition of MHC I trafficking signal or by combination with protamine. Although the efficacy of mRNA vaccines may benefit from complexing agents which protect RNA from degradation and enhance cellular uptake, cells in vivo can be transfected with mRNA in the absence of other reagents or physical transduction methods. Messenger RNA for use as a vaccine can be generated from plasmid DNA using in vitro transcription.

2. Description of Background Art

Treatment for cancers is based on the specific type that is diagnosed. Some common cancers include bladder, breast, colon, lymphoma, melanoma and prostate. Treatment regimens are prepared by physicians based on the evaluation of multiple factors including, but not limited to, disease stage, etiology and patient age and general health. For many cancers the treatment regimen can include one or a combination of surgery, chemotherapy, radiation, bone marrow/stem cell transplants, cancer drugs or immunotherapy. The most common treatments include surgery, chemotherapy, radiation and oral drugs. Although these treatments can be effective there are often many side effects. Chemotherapy in particular targets all newly dividing cells in the body not just the cancerous cells.

The advantage of some immunotherapies is the ability to target the diseased cells while leaving the non-diseased cells intact. Cancerous cells arise from a breakdown in normal growth regulatory mechanisms; therefore, the body still sees many of these cells as self. Cancer immunotherapy overcomes the body's tolerance of these diseased self-cells and allows the body to distinguish them as foreign. Cancer can also escape immune detection through direct suppression of the body's immune system by decreasing expression of immune activating markers on cells such as MHC molecules. The MHC is one of the components that help the body differentiate which cells are self and which are foreign or diseased.

Treatments for solid cancers typically include chemotherapy and/or surgery. Recently there has been interest in developing vaccines in an effort to stimulate an autologous immune defense. U.S. Pat. No. 7,795,020 describes in detail a lymphoma vaccine for treating advanced stages of lymphoma with transformed autologous or non-autologous cells isolated from a subject diagnosed with lymphoma. The isolated cells are transfected with a plasmid vector carrying a *Streptococcus pyogenes* emm55 gene. The bacterial protein is expressed on the cell surface and when the transfected cells are introduced to a subject with the cancer, generates an immunological response to lymphoma cells.

To date the FDA has approved only cellular cancer immunotherapy vaccine, Provenge, for the treatment of prostate cancer; however, some vaccines are currently being tested in clinical trials. BiovaxId is an autologous tumor derived immunoglobulin idiotype vaccine undergoing Phase III clinical studies in the treatment of indolent follicular Non-Hodgkin Lymphoma.

In principle, either exogenous DNA or RNA can express proteins in the mammalian body. Whether or not similar immune activity can be produced with both DNA and mRNA expressed proteins is uncertain. Conventional wisdom is that DNA is superior for the creation of vaccines and gene therapy due to its stability and ease of use. An example of a plasmid DNA vaccine is Merial's Oncept, which was developed for treatment of oral canine melanoma.

Work on mRNA vaccines has been reported. In one case, an effective mRNA vaccine was delivered using liposomes. This particular vaccine induced cytotoxic T lymphocytes in vivo after administration of mRNA encoding an influenza virus protein into mice. Other studies by CureVac GMH indicated that the mRNA vaccine elicits a humoral and cellular immune response upon delivery intradermally. This vaccine was administered in naked form and also complexed with protamine, a protein that enhances mRNA stability and improved protein expression. This vaccine is currently in clinical trials for castration-resistant prostate cancer.

Human trials have been performed using mRNA on liquid and solid tumors. The cancers include acute myeloid lymphoma, metastatic melanoma, prostate cancer, renal cell carcinoma/ovarian carcinoma, neuroblastoma, brain, lung, colon, and renal cell carcinoma. Most of the clinical trials that are currently being carried out involve the transfection of mRNA into autologous dendritic cells, rather than cancer cells. Additionally, no clinical trials using intratumoral administration of mRNA have been attempted. FIG. 3 is a table of published clinical trials using mRNA vaccines.

Delivery vehicles such as liposomes and cationic polymers appear to have promise in enhancing transfection. Once the liposome or polymer complex enters the cytoplasm, the mRNA must be able to separate from the delivery vehicle to enable antigen translation; unfortunately, these vehicles may not properly complex with mRNA and therefore not allow for proper translation of the encoded protein. Antigen production may occur but in amounts insufficient to produce a desired effect.

Many immunotherapies are disease-specific, complicated in concept and even more complicated and expensive to produce. It remains to be seen whether such therapies will be commercially viable. The administration of mRNA directly into a patient's tumor where it is immediately translated into an immunogenic protein which evokes a multi-tumor-antigen response has far-reaching implications. For instance, a single synthetic mRNA can be used to treat multiple types of cancer in multiple species. mRNA is simple to deliver, cost-effective, easily transported and stored, as well as easy to administer. Along with an excellent safety profile, these attributes of mRNA make it possible to treat cancer patients worldwide, even in developing countries.

Guiding the immune system to kill cancer cells is the basis for all cancer immunotherapies. In order for any type of immunotherapy to succeed, an immune response to tumor associated antigens must be triggered and allowed to amplify. The immune response can involve any number of immune cells including antigen presenting cells, neutrophils, natural killer cells, T helper cells, T cytotoxic cells and B cells, etc. However, the triggering and activation of an immune response to single tumor antigens has not proven adequate to translate into beneficial clinical efficacy in human cancer vaccine trials, most likely due to immune escape variants; nor has using whole tumor cells or tumor cell lysates plus exogenous adjuvants as a supplier of multiple relevant tumor antigens. That is why it is imperative to be able to supply the trigger in the context of the tumor antigens as they are expressed on the patient's tumor cells. The only way to accomplish this is to provide the encoding nucleic acid to the tumor cell so that the cellular machinery can express the trigger antigen alongside the tumor antigens in such a way that all of these antigens are exposed to the cells of the immune system. Such exposure then results in interantigenic epitope spreading so that an adaptive immune response is educated and activated against all tumor cells bearing those antigens, even in the absence of the trigger antigen.

Using nucleic acids as vaccines has multiple other advantages. Nucleic acid vaccines can induce both humoral and cellular immune responses; have low effective dosages; are simple to manipulate; avail rapid testing; are cost-effective and reproducible in large scale production and isolation; can be produced at high frequency and are easily isolated; are more temperature-stable than conventional vaccines; have a long shelf-life; are easy to store and transport; and are unlikely to require a cold chain.

DNA has been used in vaccines with success. DNA is a double stranded molecule that serves as the blueprint, i.e., genetic instructions, for organisms. DNA is amenable to use as a vaccine as it is fairly stable and unreactive and can be stored long term. However, DNA is self-replicating and can be easily damaged by ultra-violet radiation.

On the other hand, RNA is single stranded and functions to carry out the DNA's instructions, i.e., RNA transfers the genetic code to create proteins. RNA is more reactive than DNA and less stable but is resistant to ultra-violet radiation. As it turns out, these latter qualities make RNA better suited to use as vaccines. In general mRNA has zero chance of integrating into the host chromosomes. The delivery of mRNA results in faster expression of the antigen of interest and requires fewer copies for expression. mRNA expression is transient, which seems like a disadvantage but actually adds to its safety. mRNA is more effective than DNA for protein production in post mitotic and non-dividing cells because DNA requires translocation through the nuclear member and plasmid membrane, while mRNA requires translocation only through the plasmid membrane. mRNA is not only a template for translation, but also acts as a ligand for toll-like receptors and is nuclease sensitive; therefore it presents less concern for horizontal transmission.

SUMMARY OF THE INVENTION

The invention is based on use of a ribonucleic acid message (mRNA) (SEQ ID NO: 1, SEQ ID NO: 13, SEQ ID NO: 15 and SEQ ID NO: 16) that encodes an immunogenic bacterial protein. The message can be delivered into the cell cytoplasm using any of a number of known techniques. Once the mRNA reaches the cytoplasm, it is translated into the encoded protein using the cellular machinery already in place. The bacterial protein, such as an M-like protein having the amino acid sequence of SEQ ID NO: 2 or SEQ ID NO: 14, will then be expressed in the cell rendering immunogenicity to a cancer cell. For example, M-like proteins can be derived from the bacterial sources, Group A and G Streptococci (GAS and GGS), and therefore are seen by the mammalian body as foreign. Immune monitoring cells, such as antigen presenting cells (APCs), are attracted by the foreign protein. The APC's will phagocytize the entire cancer cell and then present all the foreign/mutant proteins including M-like protein to other immune cells.

Production of the bacterial proteins in the cells is achieved by insertion of the corresponding genetic code. The gene for M-like proteins is referred to as emmL. Once the emmL message is delivered into a cancer cell containing abnormal proteins produced by the mutation in the cell's DNA, the M-like protein will be expressed in the cell, attracting immune cells to engulf it, and lead to the presentation of the previously-masked mutated proteins to the immune system. Abnormal proteins may have been present for an extended period of time, but because they were derived from "self" proteins, the body would not necessarily view them as foreign or a threat. The bacterial protein antigen acts as a primer or trigger for the immune system to address cells that it otherwise may not have been able to identify previously as damaged and harmful.

The mRNA is produced as described in the examples. Once obtained, the mRNA containing the immunogenic message can be delivered into autologous or allogeneic cells that require the priming affect described in the summary of invention. The mRNA can also be directly delivered intratumorally or in the case of some cancers such as lymphoma, intranodally as well.

One M-like protein encoded by an emmL gene has previously been delivered into cells through DNA and has been shown to be expressed in the cell to produce an immunological effect. Due to concerns with DNA delivery, including the possibility of gene integration into the chromosomes, delivery of the message via RNA is a safer alternative because it cannot integrate into the host DNA. This ability of DNA to integrate into host DNA becomes especially relevant in medical applications where exogenous DNA integration can create detrimental effects. In contrast to DNA expression, mRNA expression lasts only a few hours to a few days at maximum inside a cell. mRNA that is not delivered into the cells is quickly degraded by RNases that are present in the environment and therefore does not pose the risk of being horizontally transmitted. When an emmL mRNA is successfully transfected into a cancer cell, it can express an immunogenic bacterial protein in the cancer cell and on its surface and thereby induce an immunogenic response.

BRIEF DESCRIPTION OF THE FIGURES

FIG. 3 is a summary of mRNA trials performed in solid cancers.

FIG. 5 shows the creation of a recombinant DNA vector to produce an mRNA encoding a bacterial antigen.

DETAILED DESCRIPTION OF THE INVENTION

Figure 1:
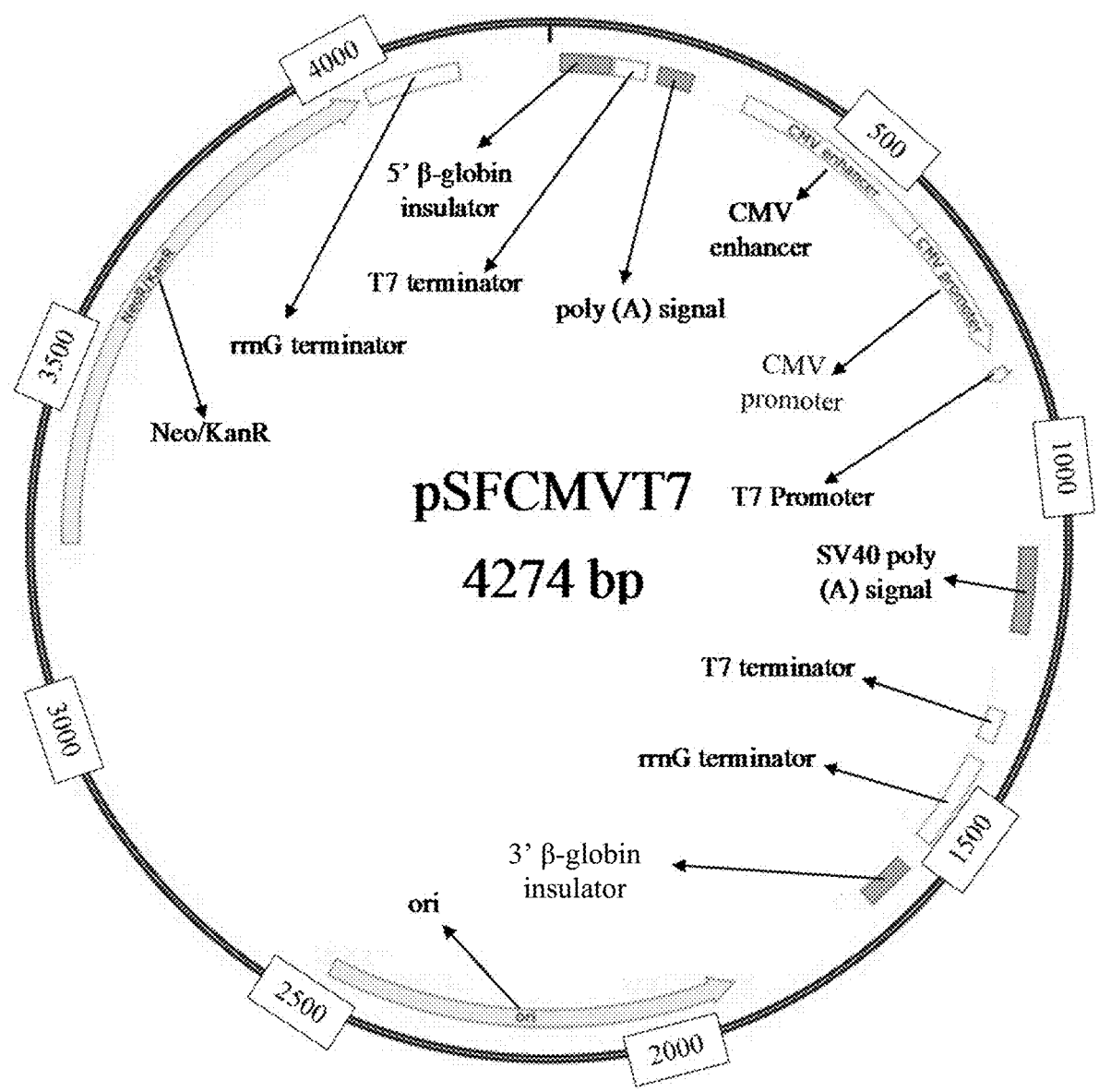
FIG. 1 illustrates the plasmid used for the backbone of the recombinant plasmid designed for mRNA production of M-like protein.

The present invention provides a cancer vaccine that can be prepared efficiently and with less expense than previously used vaccines, which are prepared by introducing plasmid DNA directly into the nucleus of the cell. The use of an emmL encoding mRNA (SEQ ID NO: 1, SEQ ID NO: 13, SEQ ID NO: 15 and SEQ ID NO: 16) inserted into the cell cytoplasm is more effective in transfecting tumor cells.

mRNA is capable of antigenic protein message delivery into cancer cells. Not only is mRNA a safer alternative because it cannot integrate into the host DNA, but also expression is limited to only a few hours to a few days at maximum. mRNA delivery also places the antigenic message further down the cellular protein production process, therefore providing a quicker expression in the cells. The mRNA only has to be delivered into the cell cytoplasm, whereas DNA must ultimately end up in the nucleus to be effective. The use of mRNA is an advantage for production of protein antigen because mRNA can induce protein production in both post mitotic and non-dividing cells.

Although mRNA delivery of antigenic proteins is a safer alternative to DNA delivery, stability and immunogenicity of mRNA must be addressed. Many of the elements that facilitate increased stability and immunogenicity were engineered into the recombinant vector template. If appropriate elements are not contained in the vector, they can be added; for example, if the template vector does not contain a poly(A) tail coding sequence, the tail is added during transcription.

In order to have increased stability in the cytoplasm, the mRNA must contain both a 5'-methylguanosine cap and a 3'-poly(A) tail (SEQ ID NO: 3). These elements are responsible for attracting and attaching the components of the cell machinery responsible for translating the mRNA into proteins. Absence of these components can decrease the time in which the mRNA is available for protein translation prior to degradation. Accordingly, these elements have been incorporated into the mRNA as described in the examples.

Efficient immunogenicity can be increased by utilization of techniques such as enhanced delivery with viral vectors, nanoparticles, cationic polymers, lipids and electroporation. Viral vectors have been used extensively in delivery of plasmid DNA (pDNA) but have several risks, as well as increased cost. Electroporation with mRNA is less toxic to cells due to less stringent electrical settings and is a preferable method for delivery of mRNA. DNA requires a higher electrical charge to pass the DNA through the outer cellular membrane and the nuclear membrane, while mRNA needs to pass only though the outer cellular membrane.

Production of mRNA for vaccines has both economic and production benefits compared to pDNA. mRNA is synthesized in vitro from a linearized pDNA template and only a small amount of DNA is required. On the other hand, production of large amounts of pDNA is labor intensive and requires equipment such as large fermentation tanks to grow sufficient bacteria to produce the massive amount of pDNA required for vaccine production. While pDNA isolated from large cultures is pure, due to the circular nature of plasmids the end product occurs in three structural forms; relaxed, linear and supercoiled. Although each form has the ability to produce an antigenic protein once inside a cell, each DNA form varies in its ability to enter the cell via the plasma membrane. Production of mRNA creates only one structural form. Moreover, due to the synthetic method of production the batch to batch reproducibility is high.

From a production standpoint, mRNA is synthesized from DNA and is highly reproducible. This is important for use as a vaccine because no large scale growth is required, i.e. it takes less time and materials and there is less risk of contamination. These factors contribute to reduced costs. Further, synthesis of mRNA leads to higher yield since it only takes one linearized plasmid DNA to yield one hundred mRNA molecules. mRNA is produced in vitro, so there is no *E. coli* contamination post isolation (genomic DNA or endotoxin). This leads to fewer purification steps and quality control tests. The synthetic nature of in vitro transcription also ensures better batch to batch reproducibility and purer product since vector sequences, including selection markers, are not part of final product. Also in contrast to DNA, mRNA has a single molecular conformation, whereas plasmid DNA has three. mRNA is also easier to transfect than plasmid DNA and results in less cell death during electroporation since lower voltage is required. Like DNA, mRNA can also be lyophilized. From a regulatory standpoint, mRNA is safer because it is non-replicating and is transient. mRNA also poses minimal to no environmental issues since it is easily degraded and confers no antibiotic resistance.

The below comparison illustrates the advantages of using mRNA instead of DNA for antigenic emmL message delivery into cancer cells. The comparison is broken up into three parts; upstream production, downstream production and cellular delivery. The bulk of the benefits, including decreased production cost, reduced manufacturing time, superior message delivery and increased safety, are seen in the upstream production and cellular delivery. Each section shows a large difference between the DNA and mRNA processes as well as similar steps for each process.

downsizing saves time and resources and decreases contamination risk. The production of the final mRNA product requires an additional step of transcribing the mRNA from the DNA template. This is a synthetic step performed in vitro. Due to the synthetic nature of transcription, there is good batch to batch reproducibility and the procedure takes only a few hours. Culturing DNA-containing bacteria can require up to several days.

A significant disadvantage of using pDNA rather than mRNA is that the end product has the potential to be contaminated with genomic DNA (gDNA). Also, the isolated pDNA forms three configurations; linear, super-coiled and circular that do not transfect cells with the same efficiency. The mRNA final product is pure, in a single conformation, and is not contaminated with gDNA or pDNA.

Chart 1 compares steps employed for DNA and mRNA production.

CHART 1

| Process Steps | DNA | Process Steps | mRNA |
| --- | --- | --- | --- |
| Vector Engineering | Designed to maximize number of plasmid DNA (pDNA) copies created in each bacterium | Vector Engineering | Designed to create a stable mRNA molecule that will lead to increased protein expression |
| Transformation of Bacteria Growth Bacterial Culture | Vector transformed into competent E. coli Transformed E. coli used to inoculate a small culture for further expansion | Transformation of Bacteria Growth Bacterial Culture | Vector transformed into competent E. coli Transformed E. coli used to inoculate a small culture for later harvesting and purification |
| Culture Expansion | Culture must be expanded to 2.5 L-1000 L depending on how much DNA is needed Depending on the desired quantity this step can add days or weeks to the process | N/A | Culture expansion not needed for mRNA because only a small quantity of DNA is needed to synthesize mRNA Approx. one linearized pDNA = 100 mRNA molecules |
| Harvesting | Large scale must be performed to generate adequate amount of DNA Labor intensive | Harvesting | Small scale due to above Saves time |
| Plasmid Isolation and Purification | End product can have a genomic DNA contamination 3 conformation of DNA produced, not all transfect efficiently | Plasmid Isolation and Purification | Small scale due to above Saves time |
| N/A | End product is purified plasmid DNA | mRNA Transcription and Purification | RNA is synthesized from linearized pDNA Once synthesized it must be purified Good batch to batch reproducibility |

Upstream Production:

The upstream production of both nucleic acid products is almost identical up to bacterial culture expansion. Only a small amount of DNA is required to produce approximately 100 times the amount of mRNA. For example, in vitro transcription experiments have yielded 25 µg of mRNA from only 0.2 µg of DNA. This is 25 times more mRNA than DNA produced using the same amount of culturing. Culture expansion can be very expensive and time consuming and leads to increase risk of contamination or mutation of DNA.

The benefit of having to grow only a small bacterial culture is significant. The small amount of DNA from this culture requires a smaller isolation to be performed. This Downstream Production (Autologous Preparation):

The majority of downstream production is the same for DNA and mRNA. One difference lies within the electroporation step. mRNA requires a lower voltage since it only has to pass through the plasma membrane and not the nuclear membrane, unlike DNA, which must pass through both the plasma and nuclear membranes. A lower voltage is favorable because it results in less cell death during electroporation. The increased viability of the mRNA transfected cells translates into an adequate proportion of vaccine cells expressing M-like proteins with ease.

Chart 2 compares processing of DNA and mRNA in tumor tissue through preparation to vaccination in transfected cells.

CHART 2

| Process Steps | DNA | Process Steps | mRNA |
|---|---|---|---|
| Specimen Arrival and Processing | Tumor tissue is excised from the patient and shipped to the laboratory If the tumor tissue is solid, it is digested using enzymes to release cells. If from lymphoma, cells are aspirated. | Specimen Arrival and Processing | Tumor tissue is excised from the patient and shipped to the laboratory If the tumor tissue is solid, it is digested using enzymes to release cells. If from lymphoma, cells are aspirated |
| Cell Cultivation | The released cells are cultured to expand total cell number, if necessary If the cell number is adequate, can proceed to transfection | Cell Cultivation | The released cells are cultured to expand total cell number, if necessary If the cell number is adequate, can proceed to transfection |
| Transfection | Must have enough voltage to pass through two membranes; plasma and nuclear | Transfection | Less voltage needed because only need to pass through the plasma membrane |
| Irradiation | Transfected cells are irradiated so they cannot divide once they are administered back into the patient | Irradiation | Transfected cells are irradiated so they cannot divide once they are administered back into the patient |
| Administration | The vaccine of irradiated cells is administered intradermally | Administration | The vaccine of irradiated cells is administered intradermally |

Cellular Delivery:

Significant advantages of using mRNA delivery are demonstrated in the cellular delivery flow chart below. As shown in the chart, mRNA delivery into the cells skips ahead to immediate translation into the antigenic M-like protein. Not only does transfected DNA have to pass through an additional cellular membrane, but it also has to be transcribed into mRNA for delivery back into the cytosol, which is the starting point for the protein synthesis initiated by the mRNA vaccine.

mRNA vaccines can be conjugated with compatible immunologic adjuvants or repressors depending on the effect desired. Adjuvants such as TriMix, a cocktail of immunostimulatory molecules, can be added to an mRNA-based vaccine eliciting an increased immune response against the encoded immunogen. Immunologic repressors can be useful to combat immunosuppressive enzymes of other elements that may hinder the body's ability to mount a sufficient immune response. These immunosuppressive elements can be silenced by using silencing RNA (siRNA) that can be co-delivered during immunization. An additional type of immune repressor that can be administered in conjunction with an mRNA based cancer vaccine is a check-point inhibitor. These generally consist of antibodies, such as anti-PD1 and anti-CTLA4, that bind to receptors present on tumor cells or immune activated cells that if left unblocked will induce immune suppression. This process has been termed as "taking off the brakes" and as it implies this release of the "brakes" allows an immunotherapy, such as the mRNA cancer vaccine, to hone the immune system efforts on attacking the cancerous cells.

The vaccine can be used not only in conjunction with checkpoint inhibitor therapy but also chemotherapy, radiation therapy, whole cell vaccines, other nucleic acid therapy, natural killer cell therapy or chimeric antigen receptor therapy prior to or concurrently with administration of the RNA vaccine.

In other cases, a cancer patient is treated with regimens that alter the tumor microenvironment, including but not limited to, cytokines, anti-fugetaxis agents, chemotactic agents and metronomic doses of chemicals prior to or concurrently with administration of the vaccine.

Chart 3 compares DNA and mRNA processing in cells from cell entry to translation.

CHART 3

| Process Steps | DNA | Process Steps | mRNA |
|---|---|---|---|
| Enter Plasma Membrane | DNA must first pass through the plasma membrane | Enter Plasma Membrane | mRNA only has to enter the cytosol to become active |
| Enter Nuclear Membrane | Next the DNA must pass through the nuclear membrane | N/A | The cellular machinery needed to process the mRNA is located outside the nucleus so this step is not required Leads to quicker protein expression |

CHART 3-continued

| Process Steps | DNA | Process Steps | mRNA |
|---|---|---|---|
| Transcription into mRNA | Once in the nucleus the DNA will be transcribed into mRNA | N/A | The step of transaction has already been accomplished previously in vitro during the upstream production |
| Exit Nucleus | After the mRNA message has been created it needs to pass back through the nuclear membrane to reach the cytosol | N/A | The mRNA never enters the nucleus so this step does not apply to mRNA |
| mRNA Translation | The mRNA is translated as soon as it reaches the cytosol | mRNA Translation | The mRNA is translated as soon as it reaches the cytosol |

In examples 23-25, mRNA encoding emmL can be produced using an in vitro transcription reaction. Several modifications to the resultant mRNA can be made in this reaction to improve mRNA and EmmL protein stability and translation efficiency, and to reduce mRNA immunogenicity. For example, a modified nucleic acid can be attached to the 5' end of emmL mRNA such as, but not limited to, anti-reverse Cap Analog [ARCA, P1-(5'-(3'-O-methyl)-7-methyl-guanosyl) P3-(5'-(guanosyl))triphosphate)], N1-methyl-guanosine, 2' fluoro-guanosine, 7-deaza-guanosine, inosine, 8-oxo-guanosine, 2-amino-guanosine, LNA-guanosine and 2-azido-guanosine.

In another example, a poly(A) tail approximately 50-200 adenosine monophosphates in length can be attached to the 3' end of emmL mRNA or both 5' modified nucleotide cap and poly(A) tail can be added to emmL mRNA.

emmL mRNA can be synthesized with ribonucleotide analogs. Chemical modifications can be made at this stage to further improve translation efficiency and stability. Examples include; 5-methyl-cytidine-5'-triphosphate, pseudouridine-5'-triphosphate, 2-thiouridine-5'triphosphate, and N1-methylpseudouridine-5'-triphosphate.

There are numerous methods to deliver mRNA to a cell such that EmmL protein will be produced at high levels. For example, emmL mRNA produced following in vitro transcription can be injected directly into a tissue or tumor.

Complexing agents such as lipids or polymers can be used to protect RNA from degradation, enhance uptake by cells and improve delivery to the translation machinery in the cytoplasm. In one embodiment, emmL mRNA is complexed with a liposome prepared from a lipophilic material such as cholesterol and synthetic phospholipids.

In one embodiment, emmL mRNA is complexed with a liposome prepared from a lipophilic material such as cholesterol and natural phospholipids.

In one embodiment, emmL mRNA is complexed with a cationic lipid such as, but not limited to, N-[1-(2,3-Dioleoyloxy)propyl]-N,N,N-trimethylammonium methyl-sulfate (DOTAP).

In one embodiment, emmL mRNA is complexed with a zwitterionic lipid such as, but not limited to, 3-[(3-Cholamidopropyl)dimethylammonio]-1-Propanesulfonate (CHAPS).

In one embodiment, emmL mRNA is complexed with a PEGylated lipid such as, but not limited to, N-(Carbonyl-methoxypolyethyleneglycol_2000)-1,2-distearoyl-sn-glycero-3 phosphoethanolamine (DSPE-PEG).

In one embodiment, emmL mRNA is complexed with a mixture of cationic, zwitterionic and PEGylated lipids.

In one embodiment, emmL mRNA is complexed with protamine.

In one embodiment, emmL mRNA is complexed with a liposome prepared from a specific material such as the Hemagglutinating virus of Japan, which has been used to prepare mRNA vaccine for the treatment of melanoma [26].

In one embodiment, emmL mRNA can be complexed with a polymer that is rationally designed with multiple materials that mimic viral components to transfect specific cells with high efficiency. These would include, but are not limited to membrane-disrupting peptides, nucleic acid binding components, a protective coat layer, and an outer targeting ligand.

In one embodiment, complexing components can be combined and formulated into a single nanoparticle.

In one embodiment, emmL mRNA or emmL mRNA complexes can be combined with interfering RNAs or interfering RNA complexes directed against immune checkpoint molecules such as programmed cell death protein 1 (PD-1), programmed death-ligand 1 (PD-L1), cytotoxic T-lymphocyte associated protein 4 (CTLA-4) or T-cell immunoreceptor with Ig and ITIM domains (TIGIT). One non-limiting example is emmL mRNA complexes and short interfering RNA (siRNA) complexes targeted to PD-1.

In one embodiment, the emmL coding region can be combined with viral RNA replication genes to form a linear RNA molecule capable of self-replication. This linear RNA molecule can then be formulated with lipophilic compounds and lipids to form liposomes capable of transfecting cells with self-replicating mRNA.

In one embodiment, emmL mRNA or emmL mRNA formulated with lipids, protamine or in liposomes, is complexed with a biodegradable polymer. One non-limiting example is polycaprolactone, which has been approved by the Food and Drug Administration for use as a drug delivery device. The advantage of biodegradable polymer complexing is that mRNA or mRNA complexes can be delivered over a long-time frame as the polymer degrades. This sustained delivery can enhance the effectiveness of a vaccine.

In one embodiment, emmL mRNA or emmL mRNA complexes can be formulated in a biodegradable polymer containing tissue- or tumor-specific factors that enhance the efficacy of the emmL mRNA vaccine. An example can be an emmL mRNA vaccine formulated with a biopolymer containing factors that inhibit angiogenesis or vasculogenesis, thereby providing a synergistic anti-tumor effect.

In one embodiment, emmL mRNA or emmL mRNA complexes can be formulated in a biodegradable polymer containing factors that reduce the expression of immune checkpoint molecules such as PD-1, PD-L1, CTLA-4 or TIGIT. As a non-limiting example, this can include existing or novel pharmaceutical reagents such as small molecules or antibodies that reduce the expression of PD-1, thereby providing a synergistic anti-tumor effect.

In one embodiment, emmL mRNA or emmL mRNA complexes can be formulated in a biodegradable polymer containing interfering RNAs or interfering RNA complexes for factors that reduce the expression of immune checkpoint molecules such as PD-1, PD-L1, CTLA-4 or TIGIT. One non-limiting example is emmL mRNA complexes and short interfering RNA (siRNA) complexes.

In one embodiment, emmL mRNA or emmL mRNA complexes can be combined with an adjuvant such as synthetic double-stranded RNA polyriboinosinic polyribocytidylic acid [poly(I:C)].

ANALYSIS OF pSFCMVT/emmL DESIGN ELEMENTS

Several design elements could improve the level of EmmL protein production.

The mRNA vaccine detailed in example 1 (SEQ ID NOs: 1-3) was cloned into the Oxford Genetics pSF-CMV_T7 plasmid DNA vector to produce pSFCMVT7/emmL. Although mRNA expression following transfection of mammalian cells was detected, only low levels of Emm55 protein were detected on western blots. A retrospective analysis of pSFCMVT7/emmL identified design elements that could improve translation efficiency in mammalian cells.

There are at least two different types of design element that could improve the level of EmmL protein production. Proximal elements are close to the emmL coding region and are added during polymerase chain reaction (PCR) amplification of emmL from pAc/emm55. Distal elements are distant from the emmL coding region and are of general utility for enhancing expression of protein from an mRNA.

Proximal elements include the introduction of a translation initiation sequence optimized for mammalian cell expression to the N-terminal end of the emmL coding region. This sequence has been determined to be RYMRMVATGGC, where R is A or G, Y is C or T, M is A or C and V is A, C or G (SEQ ID NO: 4). In one embodiment, the optimal translation initiation sequence, ATAGCCATGGC (SEQ ID NO: 5), replaces the native start codon of emmL.

In one embodiment of this proximal design element, oligonucleotide PCR primers are synthesized such that there is an equimolar concentration of each nucleotide at the degenerate positions (R, Y, M and V in SEQ ID NO: 4) and the final oligonucleotide synthesis product contains all possible primer sequences. In the current embodiment, the optimal translation initiation sequence is determined empirically by comparing the level of EmmL protein expression in assays such as western blots after the emmL gene has been sub-cloned into a mammalian expression plasmid DNA vector.

Another proximal design element that can be used to modify the C-terminal end of the emmL coding region is the addition of stop codons added after the native stop codon. Many eukaryotic expression plasmid vectors contain the DNA sequence of all three stop codon variants, TAG, TAA and TGA, immediately after the last codon of the expressed gene. Since the DNA sequence of the native emmL stop codon is TAG, SEQ ID NO: 6. can be included as an added proximal design element.

Another proximal design element is the addition of restriction endonuclease recognition sites that can be added to the N- and C-terminal ends of the emmL coding region to facilitate its insertion into plasmid cloning vectors. The choice of restriction endonuclease recognition site is made based on the destination plasmid. Some examples of restriction endonucleases that could be used are SacI, NotI, BglII, EcoRV and SpeI. In one preferred embodiment, SacI and SpeI sites are added to the N- and C-terminal ends of the emmL coding region, as they do not cut within the emmL coding region and share reaction conditions, so they can be used simultaneously to prepare the emmL coding region PCR amplimer for insertion into the destination plasmid.

Design elements that are distal to the emmL coding region are added to a plasmid cloning vector such that any variation of the emmL coding region, or other gene that is adapted with the proximal design elements, can be inserted. These distal elements can be engineered to create an mRNA expression vector capable of driving high-level mRNA and protein expression of emmL or any other mammalian mRNA.

One distal design element is the DNA sequence for a bacteriophage RNA polymerase promoter region. Examples of bacteriophage RNA polymerases are T7, T3 and SP6. In one embodiment, the promoter for T7 RNA polymerase (SEQ ID NO: 8) is the first of several distal elements added in such a way that it is ultimately upstream, with respect to the action of T7 RNA polymerase, from the emmL coding region.

RNA sequences immediately 5' and 3' of eukaryotic gene coding regions that are transcribed but not translated, termed untranslated regions (UTRs), can have strong positive or negative effects on protein translation from in vitro transcribed mRNA. In general, UTRs that support high level protein expression are unstructured, lack negative regulatory sequences and may contain the binding sites for microRNAs that serve to further refine the gene expression pattern. Both UTRs of genes that are highly expressed in mammalian cells in general, or UTRs from genes with an expression pattern matching the tissue where mRNA vaccine expression is desired, can be used to optimize delivery of a gene product such as EmmL protein. UTRs from the *Xenopus laevis* beta globin gene have been used extensively to mediate high levels of translation in a wide range of eukaryotic cells, including in the design of RNAs used for mammalian immune therapy Examples of tissue-specific UTRs are the tryptophan hydroxylase (TPH) isoforms, which drive differential expression in the pineal gland and brain stem.

In one embodiment, the *Xenopus laevis* beta globin gene 5' UTR can be positioned upstream, with respect to RNA polymerase activity, from the emmL coding region. SEQ ID NO: 9 is one non-limiting example of a *Xenopus laevis* beta globin gene 5' untranslated region.

In one embodiment, the *Xenopus laevis* beta globin gene 3' UTR can be positioned downstream, with respect to RNA polymerase activity, from the emmL coding region. SEQ ID NO: 10 is one non-limiting example of a *Xenopus laevis* beta globin gene 3' untranslated region.

In one embodiment, both the *Xenopus laevis* beta globin gene 5' and 3' UTRs can be positioned to flank the emmL coding region.

In one embodiment, 5' and 3' UTRs are selected based on the type of neoplastic cell targeted by the vaccine. In one non-limiting set of examples, the 5' and 3' UTRs of genes expressed highly in melanoma cells, such as tyrosinase (TYR), melanogenesis associated transcription factor (MITF), melanocortin receptor 1 (MC1R), telomerase (TERT), cyclooxygenase 2 (COX2), C—X—C motif chemokine receptor 4 (CXCR4) and baculoviral IAP repeat containing 5 genes (BIRC5), can be used to provide high levels of cell-specific expression to an emmL-based vaccine when used to treat melanoma.

In one embodiment, other genetic elements not located within the primary gene transcript that confer desired expression level and specificity can be included before, after or within the 5' and 3' UTRs to further refine vaccine expression.

Another distal design element is a synthetic DNA sequence that provides restriction endonuclease recognition sites that can be used to insert the emmL coding region into the other flanking distal design elements. In one embodiment, the restriction endonuclease recognition sites for SacI, NotI, BglII, EcoRV and SpeI are used (SEQ ID NO: 7).

Another distal design element is a synthetic DNA sequence that provides restriction endonuclease recognition sites to cut the destination plasmid immediately after the emmL coding region to produce a linear plasmid DNA molecule. Linearization provides effective termination for RNA polymerase activity, which increases the production of uniform length mRNA transcripts. An example of a sequence is SEQ ID NO: 11, which contains restriction endonuclease recognition sites for BamHI, EcoRI and XbaI. In one preferred embodiment, BamHI can be used to linearize a plasmid containing the emmL coding region as it does not cut within the emmL coding region and leaves a 5' nucleotide overhang, which may allow for higher efficiency transcription than a 3' nucleotide overhang.

In one embodiment, a double stranded DNA molecule containing the abovementioned distal design elements is synthesized by use of overlapping complementary synthetic single stranded oligonucleotide molecules. These molecules are annealed and gaps remaining are filled in with a DNA polymerase such as Taq polymerase.

In one embodiment, two complementary synthetic single stranded oligonucleotide molecules can be synthesized to encompass all desired distal design elements. These oligonucleotide molecules are then annealed. In either of the abovementioned embodiment, the resultant blunt-ended synthetic DNA molecule can be inserted into a PCR cloning vector such as the Invitrogen pCR® II-TOPO plasmid by adding a template non-specific adenosine. This is accomplished by incubating the blunt-ended synthetic DNA molecule with Taq polymerase and deoxyadenosine triphosphate at approximately 200 µM final concentration at 72° C. for 10 minutes.

Figure 11:
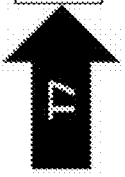
FIG. 11 is the map of a novel double stranded DNA molecule used in the production of synthetic mRNA that can be translated at high efficiency in mammalian cells. This DNA molecule contains the sequences for T7 RNA polymerase (SEQ ID NO: 8), a portion of the *Xenopus laevis* beta globin gene 5' untranslated region (SEQ ID NO: 9), a polylinker with restriction endonuclease recognition sites for SacI, NotI, BglII, EcoRV and SpeI used to insert the coding region of emmL (SEQ ID NO: 7), a portion of the *Xenopus laevis* beta globin gene 3' untranslated region (SEQ ID NO: 10), then a polylinker with restriction endonuclease recognition sites for BamHI, EcoRI and XbaI used to linearize the plasmid prior to in vitro transcription (SEQ ID NO: 11). The DNA sequence corresponding to FIG. 11 is SEQ ID NO: 12.

In one embodiment, a plasmid containing the abovementioned distal design elements is named pT7XLUTR. A map of the synthetic DNA molecule inserted into pCR®II-TOPO is shown as FIG. 11 and the nucleotide sequence is shown as SEQ ID NO: 12. This sequence contains the abovementioned distal design elements, but does not represent the totality or full extent of elements that could be added to support the desired expression level or specificity.

pT7XLUTR can be used to transform E. coli. Bacterial transformed with pT7XLUTR can be selected on an agar plates containing an antibiotic that matches the PCR cloning vector, such as agar plates containing Luria Bertani broth supplemented with 50-100 µg/mL kanamycin or carbenicillin. The bacterial culture can be expanded by growth in a liquid antibiotic selective media, such as Luria Bertani broth supplemented with 50-100 µg/mL kanamycin or carbenicillin, and plasmid DNA prepared using methods known to a person practiced in the art.

EXAMPLES

The following examples are provided as illustrations of the invention and are in no way to be considered limiting.

Example 1. Autologous mRNA Vaccine for Canine Lymphoma

A 75 lb. male neutered Rhodesian Ridgeback, presents to his veterinarian with swollen mandibular and inguinal lymph nodes. The patient has a fine needle aspirate performed on one of the enlarged nodes. Upon review by the pathologist he is diagnosed with low grade diffuse lymphoma.

The patient's owner elects to pursue immunotherapy treatment instead of chemotherapy and steroids, due to the minimal side effects reported in immunotherapy treatments. The veterinarian excises the right mandibular lymph node while the patient is under general anesthesia. The tissue sample is shipped overnight for laboratory processing.

Upon receiving the tissue sample at the lab the following is performed: 1) the travel medium is checked for any bacterial contamination, 2) the tissue dimensions are measured, 3) the intact lymph node is aspirated repeatedly using several boluses of wash medium to release the tumor cells, and 4) the aspirated cells are collected and counted.

An appropriate amount of cells is made available to electroporate with emmL encoding mRNA. Using a BioRad Gene Pulse machine, $120 \times 10^6$ cells are transfected with 80 µg of mRNA. A small portion of the transfected cells are cryopreserved, while the rest are placed in culture for approximately 24 hours. After 24 hours the cells are irradiated and aliquoted into $10 \times 10^6$ cell vaccine doses that are cryopreserved until needed.

The patient is administered a total of 8 vaccine doses. Each dose is shipped overnight from the laboratory to the veterinary clinic, arriving on the scheduled administration day. The veterinarian administers each dose intradermally using a syringe with needle. The 8 vaccine doses are given every 7 days (+/−1 day) for 4 weeks and then once a month for 4 months. Prior to the first dose a blood sample is taken. Subsequent blood samples are taken preceding the $5^{th}$ vaccine, $8^{th}$ vaccine and 8 weeks after the last vaccine. The blood samples are processed for peripheral blood & plasma and preserved at the lab. They are later used for evaluation of anti-tumor immune response.

Throughout the course of treatment, the patient's lymph node size is monitored along with his overall quality of life. Overall disease state is assessed by tumor burden reduction and anti-tumor immune response. Tumor burden is evaluated through measurements performed on each of the lymph nodes throughout the course of treatment. Anti-tumor immune response is measured using standard enzyme-linked immunosorbent assay (ELISA) to assess antibody levels and flow cytometry to assess cytotoxic T-cell (CTL) response.

During the course of treatment, the patient's lymph node size increases and later decreases as the course continues. This observation is probably due to infiltration of immune cells into the tumor site, in this case, the lymph nodes. The ELISA and flow cytometry results show an increase in antibody production and CTLs after the fourth vaccine that then persists after the completion of the series of vaccines.

Example 2. Direct mRNA Vaccine for Equine Melanoma

A 15 year old Andalusian, presented to her veterinarian with black lesions on her neck, mane and in the perianal area. Upon review of a fine needle aspirate the pathologist diagnoses the patient with melanoma. The owner elects to pursue immunotherapy treatment due to the complicated nature of excising the perianal lesion on the patient.

Three vaccine doses are prepared containing 100 μg mRNA in 100 μL sterile nuclease free $H_2O$. The three doses and three needle-free injection devices (J-Tip) are shipped to the veterinarian. Three of the patient's lesions are chosen to receive the treatment course, a total of 300 μg mRNA per time point. Every two weeks three more doses are shipped to the veterinary clinic as previously done and each dose is administered to the same three lesions using the J-Tip device. The patient receives a total of six vaccine doses per lesion.

Blood samples are collected prior to initiation of the vaccine series, prior to the $5^{th}$ vaccine dose and two weeks after the series is completed. The blood samples are processed for peripheral blood & plasma and preserved. They are later used for evaluation of anti-tumor immune response.

Overall disease state is assessed by tumor burden reduction and anti-tumor immune response. Tumor burden is evaluated through measurements performed on the lesions before each of the six vaccine doses are administered. Anti-tumor immune response is measured using standard ELISA to assess antibody levels and flow cytometry to assess the CTL response.

As seen in other patients receiving immunotherapy treatment, the melanoma lesions will initially increase in size followed by a decrease as the vaccine series progresses. The ELISA and FACS results show an increase in antibody production and CTLs after the second vaccine that will persist after the completion of the series of vaccines.

Example 3. Overview of Methods for emmL mRNA Creation

Methods Overview:

Restriction Enzyme Digestion of Vector and Insert

Figure 2:
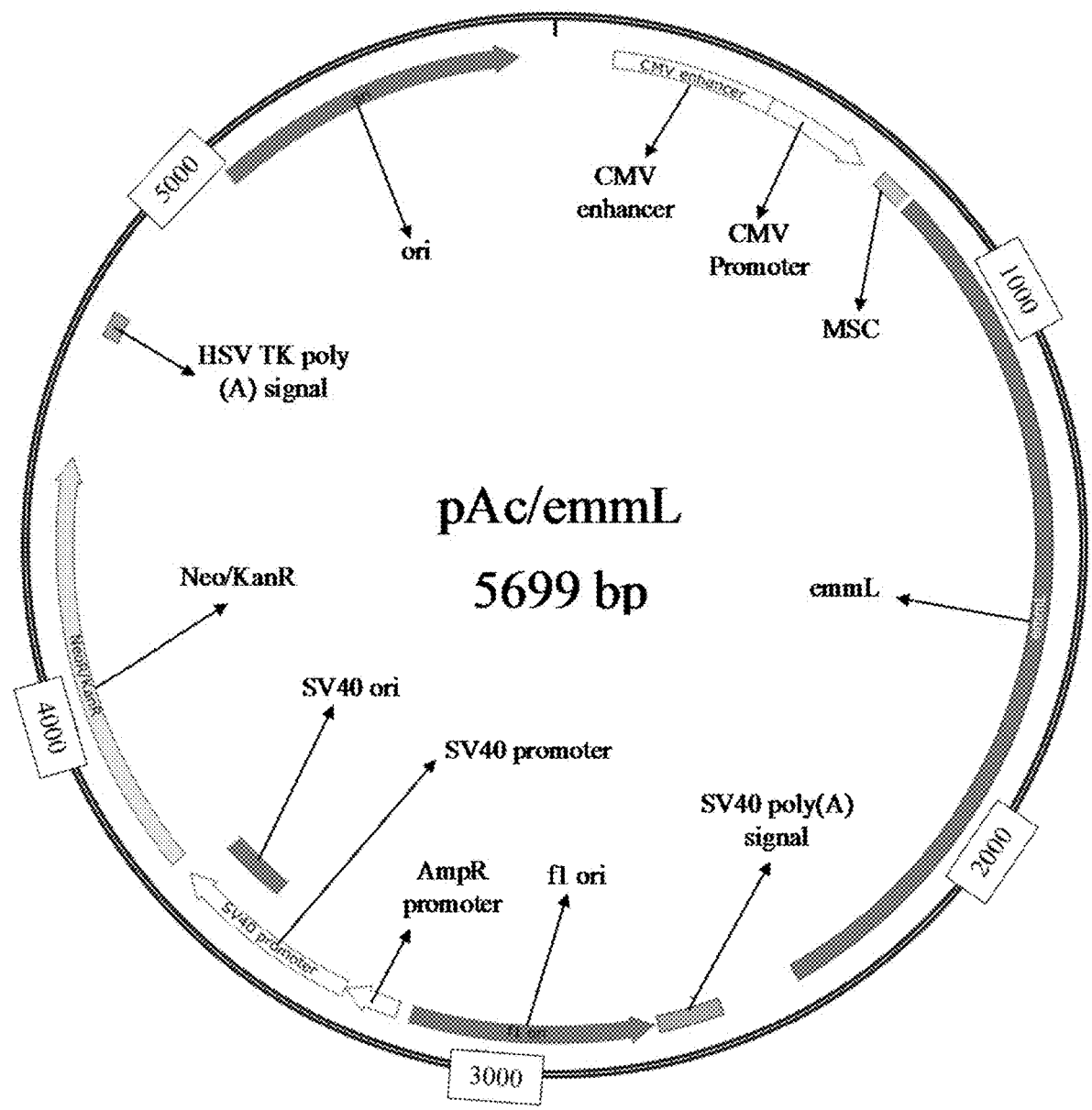
FIG. 2 illustrates the plasmid DNA used as the source for the emmL gene to be ligated into the linearized vector of FIG. 1.
Figure 4:
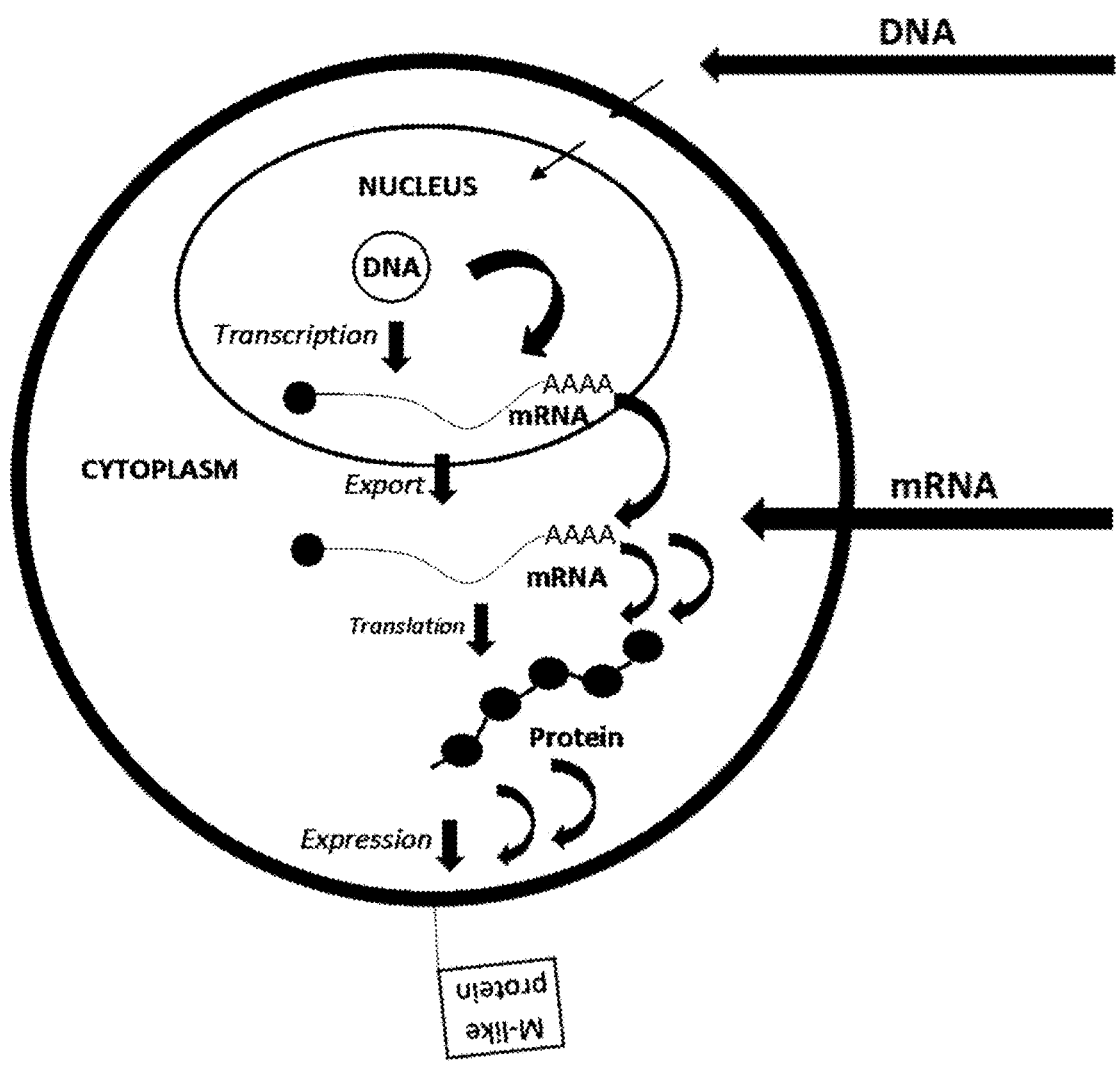
FIG. 4 is a diagram demonstrating the cellular production pathway differences between mRNA and DNA.

To create the appropriate recombinant plasmid for optimal mRNA production, a plasmid backbone including dual prokaryote and eukaryote promoters, untranslated 3' and 5' regions, and a selective marker was used. A vector of this type; for example, pSFCMVT7, has multiple features that aid in the production and stabilization of the mRNA encoding an antigenic M-like protein, such as Emm55. Both the vector pSFCMVT7 and the insert containing plasmid pAc/emmL were cut using restriction enzymes SacI and EcoRV. Refer to FIGS. 1 and 2 for plasmid maps.

DNA Fragment Separation with Gel Electrophoresis

Once the restriction digestion was performed with the appropriate enzymes, the DNA fragments were isolated through gel electrophoresis. A reference DNA ladder is run with both the digestion reactions to assess DNA band lengths, thus aiding in identification of the bands of interest. The bands containing the DNA were extracted from the gel.

Gel Extraction/DNA Isolation

The gel slices containing the DNA of interest were solubilized and the DNA extracted in order for the vector and insert to be ligated together to create the recombinant plasmid pSFCMVT7/emmL.

Vector and Insert Ligation

During the restriction digestion of the vector and insert containing plasmids, "sticky ends" were created, which were pieced together later with a ligation reaction. The "sticky ends" refer to unpaired nucleotides that are available for hydrogen bonding with the complementary nucleotides. Since the vector pSFCMVT7 and insert emmL were cut with the same restriction enzymes they contain complementary ends that were joined upon exposure to T4 DNA ligase.

Transfection into Bacteria

After the mRNA production plasmid pSFCMVT7/emmL was created, it was transformed, i.e., transfected, into competent bacteria that produce sufficient DNA that was isolated and will be used for in vitro mRNA synthesis. Invitrogen's Stbl3 *E. coli* is an example of the type of bacteria that can be used for transfection. Transformation was induced by heat shocking the bacteria to open up small orifices in the cell membranes allowing the plasmid to enter the cell and ultimately the nucleus.

Growth and Expansion of Bacterial Culture

The bacteria transfected with the plasmid were placed onto appropriate growth medium containing a selective antibiotic. In the case of pSFCMVT7 this is a kanamycin. If the bacteria are correctly transformed with the plasmid they will produce a protein that will hinder the anti-bacterial properties of the kanamycin and allow the kanamycin-resistant bacteria to selectively grow on the medium.

Plasmid Isolation and Purification

Once an adequate number of bacteria containing pDNA had grown, the cells were lysed allowing for the plasmid to be released from inside the cells. The pDNA was isolated from the gDNA, proteins and other cellular debris through filtration and an anionic exchange column.

Preparation of Template DNA: Plasmid DNA Linearization

The isolated DNA contains the template DNA for mRNA production. In order for the transcription reaction to occur, the plasmid must be linearized. It is important that the linearization occur down-stream from the open reading frame gene of interest.

mRNA Transcription Reaction

After the template has been prepared, the message is created through an in vitro transcription reaction. This reaction simulates the transcription of mRNA in the cell, including the capping of the 5' end and addition of a poly(A) tail for increased stabilization.

mRNA Purification

Once the message has been transcribed into mRNA, the residual DNA template is degraded so that a pure mRNA product can be used to transfect into autologous cells, allogeneic cells or intratumorally. Once inside the cells the mRNA will produce and display the M-like protein on the cell surface for immune activation.

Transfection of Cancer Cells with mRNA

One way the mRNA can be delivered into the cancer cells is by the method of electroporation. This method utilizes a weak electrical current that causes the cellular membrane to open up small pores that then allow the mRNA to move through the membrane and into the cytoplasm.

Example 4. Restriction Enzyme Digestion

Table 1 shows the procedure for rapid digestion of pDNA.

TABLE 1

| STEP | | | |
|---|---|---|---|
| 1 | Set up two reactions as follows, each in a separate 0.5 mL tube: | | |
| | | pSFCMVT7 (Vector) | pAc/emmL (Insert) |
| | Sterile, nuclease-free water | To 50 μL | To 50 μL |
| | RE 10X Buffer | 5.0 μL | 5.0 μL |
| | Acetylated BSA (10 μg/mL) | 0.5 μL | 0.5 μL |
| | DNA (5 μg) | 5 μg | 5 μg |
| | SacI (10 μg/μL) | 3.0 μL | 3.0 μL |
| | EcoRV (10 μg/μL) | 3.0 μL | 3.0 μL |
| | Total Volume | 50.0 μL | 50.0 μL |
| 2 | Mix reaction well by pipetting up and down gently. | | |
| 3 | Pulse centrifuge all the tubes to get the entire contents to the bottom. | | |
| 4 | Incubate in dry heating block at 37° C. for 1 hour. | | |
| 5 | Run gel electrophoresis to separate fragments. | | |

Example 5. DNA Fragment Separation with Gel Electrophoresis

Table 2 shows the procedure for DNA fragment separation.

TABLE 2

| STEP | |
|---|---|
| 1 | Dissolve 1.0% agarose in 50 mL of 1X TAE buffer by heating in the microwave. Ok it boils. Ensure all granules have solubilized. |
| 2 | Cool flask with liquid agar under running tap water. |
| 3 | Pour liquid agar into gel cast with comb making sure not to create any bubbles |
| 4 | Allow gel to solidify at room temperature. |
| 5 | While gel is cooling, Create 1 kb ladder solution by adding 10 μL Promega 1 kb ladder and 2 μL dye in a microcentrifuge tube. |
| 6 | Add 2 μL Blue juice to each reaction. |
| 7 | Load 12 μL of 1 kb ladder and 50 μL of each reaction into gel. |
| 8 | Run gel at 80 volts until samples move out of the gel wells, then increase to 100 volts until dye reaches the bottom of gel. |
| 9 | Take picture of gel using bioimaging equipment with ultraviolet light. Do not expose the gel to the UV light more than 1 minute to prevent mixing of the DNA. |
| 10 | Cut out bands of interest pSFCMVT7 vector (~4234 bp) and emmL (~1700 bp) using a sterile scalpel and store at −20° C. until needed. |

Example 6. Gel Extraction/DNA Isolation

Table 3 shows the procedure for Extraction and DNA Isolation.

TABLE 3

| STEP | |
|---|---|
| 1 | Minimize the size of the gel slice by removing extra agarose with a scalpel. |
| 2 | Weight gel slices. |
| 3 | Add 3 volumes of gel solubilization buffer to 1 volume of gel to each. |
| 4 | Incubate at 50° C. for 10 minutes (or until the gel slice has completely dissolved). Mix by vortexing every 2-3 minutes to help dissolve gel. |
| 5 | After gel slice appears dissolved, incubate the tube for an additional 5 minutes. |
| 6 | Add 1 gel volume of isopropanol to the sample and mix. |
| 7 | Place a gel extraction column in a provided 2 mL collection tube for each sample. |
| 8 | Apply samples (maximum capacity 700 μL, meaning more than one centrifugation may need to be performed) from step 6 to the labeled columns and centrifuge at >12,000 x g for 1 minute. |
| 9 | Discard flow-through by pipetting contents out of tube, carefully avoiding leaving droplets on sides of tubes, and place column back in the same 2 mL collection tubes. |
| 10 | Add 0.5 mL of wash buffer to the columns and centrifuge at >12,000 x g for 1 minute. |
| 11 | Repeat Steps 9 and then 10. |
| 12 | Repeat Step 9 and then proceed to Step 13. |
| 13 | Remove excess buffer by centrifuging the tubes at >12,000 x g for 1 minute and repeat Step 9. |
| 14 | Remove excess ethanol by centrifuging the tubes at >12,000 x g for 3 minutes and repeat Step 9. |
| 15 | Place columns in clean 1.5 mL microcentrifuge tube. |
| 16 | Elute DNA by adding 50 μL of elution buffer to the center of each column's membrane and centrifuge for 1 minute at >12,000 x g. |
| 17 | Use spectrophotometer to measure the DNA concentration in each sample. Use these numbers to calculate the quantity of vector and insert needed for ligation. |

Example 7. Vector and Insert Ligation

Table 4 shows the procedure for vector insert and ligation.

TABLE 4

| STEP | | | |
|---|---|---|---|
| 1 | Use the following equation to calculate the quantity of vector and insert needed for ligation (use molar ratio of 1:2 vector to insert): | | |
| | $$\frac{\text{ng of vector} \times \text{bp size of insert}}{\text{insert bp size of vector}} \times \text{molar ratio of insert} = \text{ng of insert vector}$$ | | |
| 2 | Set up the following reactions in microcentrifuge tubes on ice: | | |
| | | Sample | Negative Control (vector only) |
| | 2X Rapid Ligation Buffer | 5 μL | 5 μL |
| | Vector DNA | Calculate | Calculate |

TABLE 4-continued

| Insert DNA | Calculate | n/a |
| Nuclease-free water | To 10 μL | To 10 μL |
| T4 DNA Ligase | 1 μL | 1 μL |
| Total volume | 10 μL | 10 μL |

| | |
|---|---|
| 3 | Gently mix the reaction by pipetting up and down. Pulse centrifuge. |
| 4 | Incubate at 4° C. overnight (at least 12 hours). |
| 5 | Proceed to Transformation of Stbl3 *E. coli* protocol. |

Example 8. Transformation of DNA into *E. coli*

Table 5 shows the procedure for transformation of *E. coli*.

TABLE 5

| STEP | |
|---|---|
| 1 | Thaw three tubes of *E. coli* in an ice bath immediately before using. |
| 2 | Label these tubes ligation, positive control and negative control. Negative control consists of vector only from ligation protocol. Positive control consists of the original intact plasmid. Ligation consists of the newly constructed plasmid. |
| 3 | Add 10 pg to 100 ng of the corresponding DNA to each tube. |
| 4 | Incubate tubes in an ice bath for 30 minutes. |
| 5 | Heat shock cells for 45 seconds at 42° C. |
| 6 | Return to the ice bath for 2 minutes. |
| 7 | Add 250 μL SOC medium to each tube (pre-warmed to 37° C.). |
| 8 | Cap vials tightly and shake horizontally at 37° C. and 225 rpm for 1 hour. |
| 9 | Plate 25 μL and 100 μL of each transformation, at 100% and 1:10 dilution in LB medium, onto LB with kanamycin agar plates. |
| 10 | Store remaining mix at 4° C. in case additional cells need to be plated the following day. |
| 11 | Invert and incubate the plates overnight at 37° C. |
| 12 | The following day count colonies and calculate transformation efficiency using the following equation.<br><br>$$\frac{\text{\# of colonies}}{\text{X pg DNA}} \times \frac{10^6 \text{ pg}}{\mu g} \times \frac{\text{X } \mu L \text{ total volume}}{\text{X } \mu L \text{ plated}} \times \text{dilution factor} =$$<br><br>transformation efficiency(# transformants/μg DNA)<br><br>The efficiency should exceed $1 \times 10^8$ cfu/μg plasmid. |
| 13 | Select colonies for further expansion and characterization. |

Example 9. Growth and Expansion of Bacterial Culture

The Table 6 shows the procedure for growth and expansion of the bacterial culture.

TABLE 6

| STEP | |
|---|---|
| 1 | Select one colony from agar plate and place in culture tube with 5 mL LB broth containing kanamycin. |
| 2 | Place in 37° C. shaking incubator at 300 rpm overnight. |
| 3 | After 8-12 hours measure OD 600. When reaches 8.0 AU centrifuge bacteria and proceed according to plasmid isolation protocol. |

Example 10. Plasmid Isolation and Purification

Table 7 shows the procedure for plasmid isolation and purification.

TABLE 7

| STEP | |
|---|---|
| 1 | Add LyseBlue reagent (one vial) to Buffer P1 and mix to yield a 1:1000 dilution. Use a sterile biological hood to add reagent. |
| 2 | Add RNase A solution (one vial) to Buffer P1 to yield a final concentration of 100 μg/mL. Use a sterile biological hood to add solution. |
| 3 | Pre-chill Buffer P1 and Buffer P3 in 4° C. refrigerator. |
| 4 | Prepare 70% ethanol by adding 3.5 mL 100% ethanol to 1.5 mL nuclease-free water. |
| 5 | Check Buffer P2 for SDS precipitation. If necessary dissolve SDS by warming to 37° C. Leave Buffer P2 bottle closed when not in use to avoid acidification from $CO_2$ in air. |
| 6 | Harvest the bacterial cells by centrifugation at 2773 × g for 30 minutes at 4° C. using the Beckman centrifuge. If you wish to stop the protocol and continue later, freeze cell pellets at −20° C. |

TABLE 7-continued

| STEP | |
|---|---|
| 9 | Decant supernatant and resuspend bacterial pellet in 0.3 mL of chilled Buffer P1 (vigorously shake bottle to mix before adding to the pellet). The pellet should be completely resuspended by pipetting up and down to ensure complete mixing of lysis buffer. |
| 10 | Add 0.3 mL of Buffer P2, mix by gently inverting four to six times, and incubate at room temperature for five minutes. The solution should turn blue. |
| 11 | Add 0.3 mL of chilled Buffer P3 and mix thoroughly by inverting four to six times. The solution should turn colorless with a fluffy white precipitate. |
| 12 | Incubate on ice for 5 minutes. |
| 13 | Centrifuge at 14,000-18,000 x g for 10 minutes. Remove supernatant containing plasmid DNA. |
| 19 | Equilibrate a QIAGEN-tip 20 by applying 1 mL buffer QBT and allow the column to empty by gravity flow. |
| 20 | Apply supernatant from step 13 to the QIAGEN-tip 20 and allow column to empty by gravity flow. |
| 21 | Wash the QIAGEN-tip 20 with 2 × 2 mL buffer QC. |
| 22 | Elute DNA into a clean 1.5 mL microcentrifuge tube by adding 0.8 mL Buffer QF to the column. |
| 23 | Precipitate DNA by adding 0.7 volumes (590 μL per 800 μL of elution volume) of room-temperature isopropanol to the eluted DNA. |
| 24 | Mix and centrifuge immediately at 15,000 x g for 30 minutes. Decant supernatant. |
| 25 | Wash DNA pellet with 1 mL of 70% ethanol and centrifuge 15,000 x g for 10 minutes. Decant supernatant. |
| 26 | Air-dry pellet for 15-30 minutes and re-dissolve in suitable volume of TE buffer. Ideal final concentration is 1 mg/mL or less. |
| 26 | Measure yield of plasmid DNA following |
| 27 | Store sample at −80° C. |

Example 11. Preparation of Template DNA

Table 8 shows the procedure for preparation of template DNA and plasmid linearization.

TABLE 8

| STEP | |
|---|---|
| 1 | Add the following to a Biopur tube (2 mL): 40 μL 10X restriction enzyme buffer, 4.0 μL BSA, 5 μg of plasmid DNA, and sterile nuclease-free water up to a final volume of 390 μL. |
| 2 | Mix by gently pipetting up and down. |
| 3 | Add 10 μL of restriction enzyme BamHI. |
| 4 | Incubate at 37° C. for 1-2 hours. |
| 5 | Terminate the digestion by adding the following into the tube in sequential order: 20 μL of 0.5M EDTA, 40 μL of 3M NH$_4$OAc, and 800 μL ethanol. |
| 6 | Mix and chill at −20° C. for 15 minutes. |
| 7 | Centrifuge the tube to pellet the DNA for 15 minutes at 16,000 x g and 4° C. |
| 8 | Decant the supernatant and pulse centrifuge. |
| 9 | Remove the remaining supernatant with a fine-tipped pipette. |
| 10 | Resuspend the DNA in nuclease-free water or TE buffer to yield a final concentration of 0.5 μg-1.0 μg/μL. |

Example 12. mRNA Transcription

Table 9 shows the procedure for transcribing mRNA.

TABLE 9

| STEP | |
|---|---|
| 1 | Thaw all frozen reagents. |
| 2 | Place RNA Polymerase Enzyme Mix on ice. |
| 3 | Vortex 10X T7 Reaction Buffer and T7 2X NTP/ARCA to ensure they are completely mixed. Place T7 2X NTP/ARCA on ice and leave 10X T7 Reaction Buffer at room temperature. |
| 4 | Set up the following reaction at room temperature: |

TABLE 9-continued

| STEP | | |
|---|---|---|
| | Sample | |
| | Nuclease-free water | To 20 μL |
| | T7 2X NTP/ARCA | 10 μL |
| | 10X T7 Reaction Buffer | 2 μL |
| | Linearized plasmid DNA | 0.5 μg |
| | T7 Enzyme Mix | 2 μL |
| | Total volume | 20 μL |
| 5 | Mix gently by pipetting up and down. Pulse centrifuge. | |
| 6 | Incubate at 37° C. for 1 hour. | |
| 7 | Add 1 μL of TURBO DNase and mix well. | |
| 8 | Incubate at 37° C. for 15 minutes. | |
| 9 | To the 20 μL reaction add the following: 36 μL nuclease-free water, 20 μL 5X E-PAP Buffer, 10 μL 25 mM MnCl$_2$, and 10 μL ATP solution. | |
| 10 | Pull 2.5 μL and set aside for gel. | |
| 10 | Add 4 μL E-PAP and mix gently. | |
| 11 | Incubate at 37° C. for 30-45 minutes. | |
| 12 | Place reaction on ice until needed for purification reaction. | |

Example 13. mRNA Purification

Table 10 shows the procedure for purifying the mRNA.

TABLE 10

| STEP | |
|---|---|
| 1 | Bring RNA sample to 100 μL with elution solution. Mix gently by pipetting up and down. |
| 2 | Add 350 μL binding solution concentrate to the sample and mix gently by pipetting up and down. |
| 3 | Add 250 μL of 100% ethanol to the sample and mix gently. |
| 4 | Insert a filter cartridge into the collection tube. |
| 5 | Add mRNA mixture to the filter cartridge. |
| 6 | Centrifuge for 1 minute at 10,000-15,000 x g. Make sure the entire mixture has passed through the filter at the end of the centrifugation. |
| 7 | Discard the flow-through and place filter back in the tube. |
| 8 | Add 500 μL wash solution and repeat step 6 and 7. |
| 9 | Repeat Step 8. |
| 10 | Pulse centrifuge the filter one more time to remove any residual wash solution. |
| 11 | Place filter in a new collection/elution tube. |
| 12 | Apply 50 μL of elution solution, close the tube cap and incubate in a heat block at 65-75° C. for 5-10 minutes. |
| 13 | Recover eluted mRNA by centrifuging for 1 minute at 10,000-15,000 x g. |
| 14 | Measure purity and quantity using a spectrophotometer. |

Example 14. Transfection of Cancer Cells with mRNA

Table 11 below shows the procedure for transfection of mammalian cancer cells with emmL mRNA.

TABLE 11

| STEP | |
|---|---|
| 1 | Assess the viability of the cell suspension using Trypan Blue dye exclusion. |
| 2 | For transfection collect 15 × 10$^6$ cells in a 15 mL conical tube. Centrifuge cells at 638 x g and 10° C. for 10 minutes. |
| 3 | Decant supernatant and add 10 mL DPBS. Centrifuge cells at 638 x g and 10° C. for 10 minutes. |
| 4 | Repeat Step 3 two more times. |

TABLE 11-continued

| STEP | |
|---|---|
| 5 | Resuspend cells in 300 µL transfection buffer. Mix gently using a pipette and then transfer suspension to 0.4 cm electroporation cuvette. |
| 6 | Add 20 µg mRNA to cell suspension in cuvette. Mix gently using pipette. |
| 7 | Set gene pulser to 260 v and 750 µF. Load cuvette and pulse. |
| 8 | Transfer electroporated cells in cuvette to T-75 flask with 20 mL of medium. |
| 9 | Place flask in incubator at 37° C. and 5% $CO_2$ overnight. |
| 10 | After 24 hours assay for expression of M-like protein on cancer cell surface. |

Example 15. Cloning Steps for DNA pSFCMVT7/emmL

FIG. 5 shows the procedure for creating a recombinant DNA vector to produce mRNA encoding bacterial antigen.

Example 16. Direct Binding of Antibody to M-Like Protein

Figure 6:
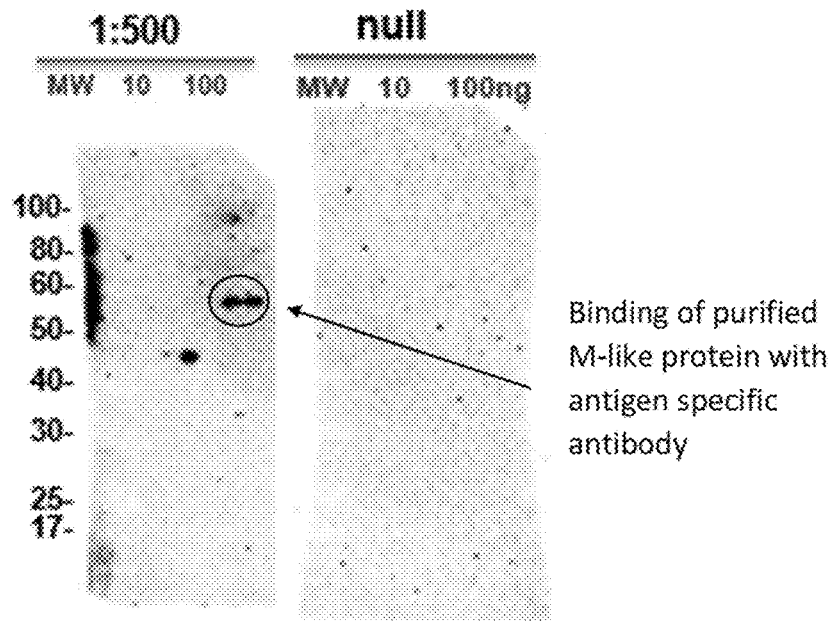
FIG. 6 shows a Western blot of isolated Emm55 against an anti-M-like antibody.

The Western blot shown in FIG. 6. demonstrates the specificity of the anti-M-like protein antibody to isolated M-like protein, specifically Emm55.

Proteins were separated by SDS-PAGE (10%) using 130 mM β-ME in the loading buffer. Samples were boiled for 3 minutes at 100° C. and spun at 13,000×g for 2 minutes at room temperature. The blots (far left) were probed with primary antibody (α-M-like Protein) for 1.5 hours at room temperature in 5% milk. The primary antibody dilution was 1:500. The secondary antibody (goat α-mouse conjugated HRP) was at a dilution of 1:5000. The null blot (second from left) shows the non-specific binding of secondary antibody.

Chemiluminescence was used to visualize the protein on the nitrocellulose blots (exposure: 10 minutes).

Example 17

Figure 7:
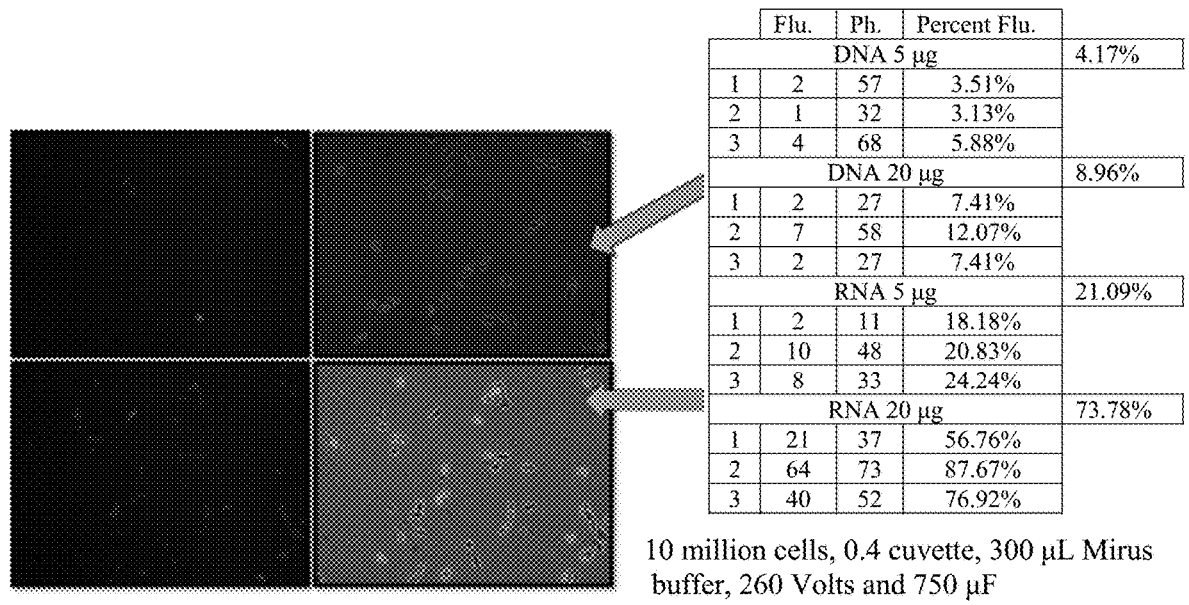
FIG. 7 shows comparative results of protein expression from DNA and RNA transfection.

Fluorescence microscope images and chart demonstrating the increased expression seen with mRNA as compared with DNA. Results were compared from an experiment in which RNA and DNA were transfected into mammalian cells and assayed for protein expression. The results show that RNA at equivalent transfection quantity produced five times the amount of expression. (See FIG. 7).

Example 18. Synthesized emmL mRNA, Untailed and Tailed

Figure 8:
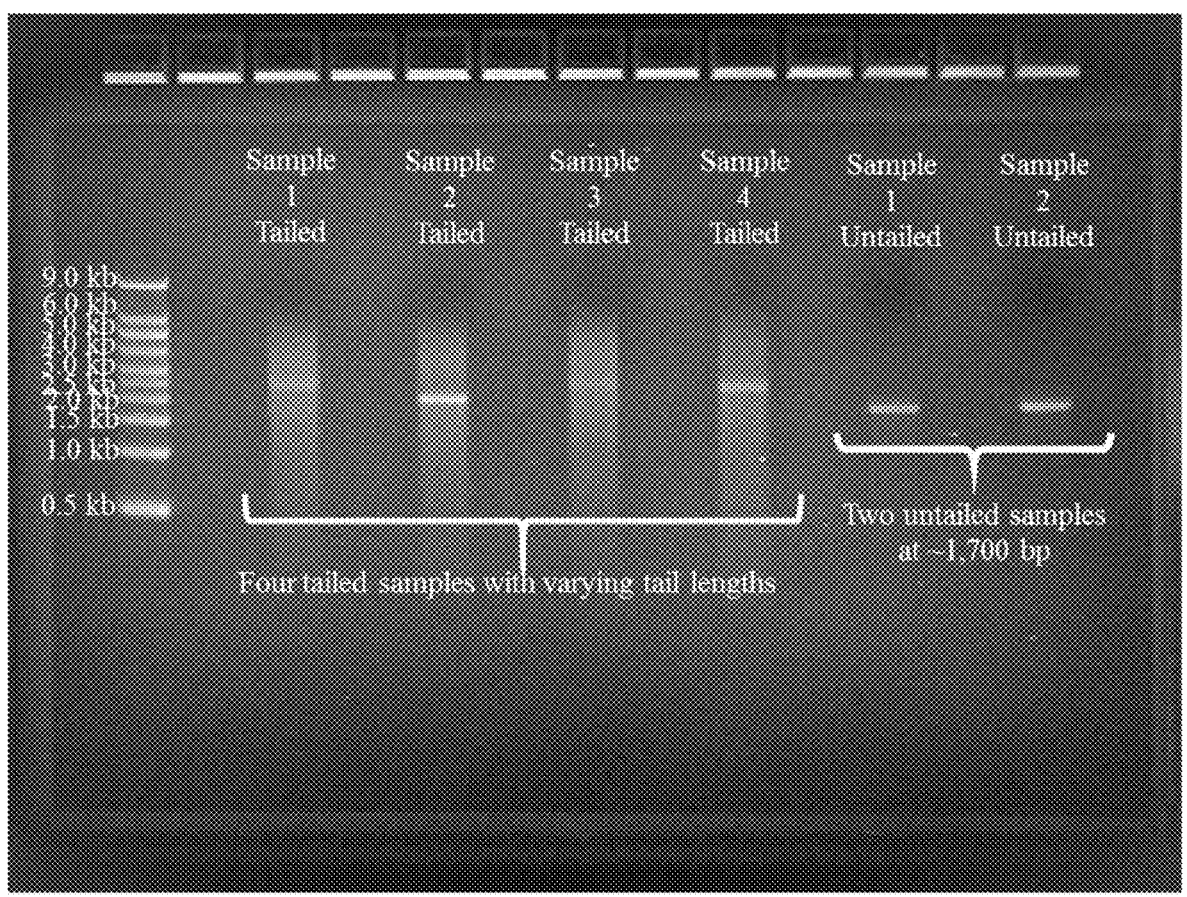
FIG. 8 is a photograph of an agarose gel of synthesized emm55 mRNA using a Flashgel system.

The procedure used to perform the denaturing agarose gel shown in FIG. 8 demonstrates the visualization of the synthesized emmL mRNA, specifically emm55 mRNA using the Lonza FlashGel system.

20 ng samples and 100 ng ladder were prepared by diluting the total quantity into a 2.5 µL volume using DEPC treated water. An equivalent volume of formaldehyde sample buffer was added to each sample. The samples were mixed and then incubated at 65° C. for 15 minutes followed by a 1 minute incubation on ice. Samples were loaded into a 1.2% RNA gel cassette and then run at 225 volts for 8 minutes. The gel was incubated at room temperature for 10 minutes and then visualized using the FlashGel camera. mRNA sizes are determined by the RNA Millennium Marker.

Example 19

Chart 4 displays the results from an experiment in which RNA (emmL mRNA) and DNA (pSFCMVT17/emmL) were transfected into mammalian cells, stained with α-M-like protein, and assayed using flow cytometric analysis. The results show that the RNA-transfected cells produce an equivalent signal to the DNA transfected cells, i.e. 9%.

CHART 4

| Tube Treatment | % Parent | Minus Unstained | Minus Stained Untransfected |
|---|---|---|---|
| Unstained | | | |
| Untransfected | 1 | | |
| emmL mRNA | 0.4 | | |
| pSFCMVT17/emmL | 1.9 | | |
| Stained | | | |
| Untransfected | 5.6 | 4.6 | −1 |
| emmL mRNA | 14.8 | 14.4 | 9 |
| pSFCMVT17/emmL | 16.6 | 14.7 | 9 |

Example 20

Figure 9:
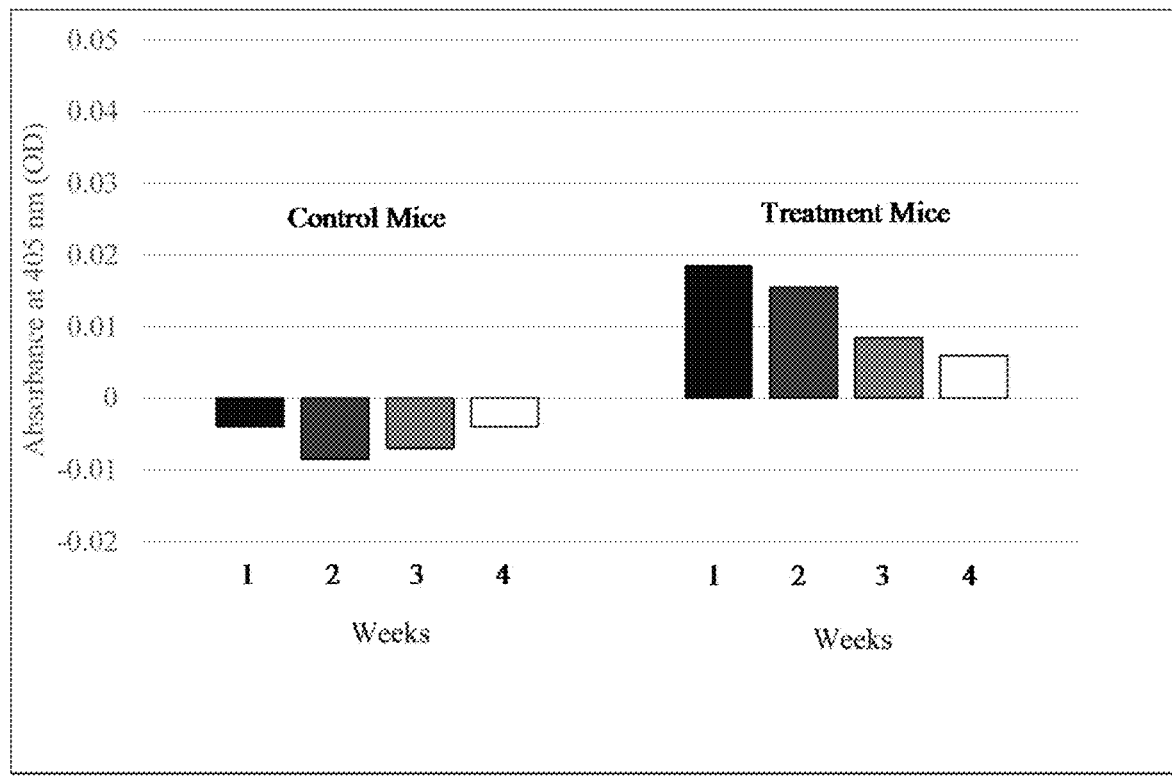
FIG. 9 is a graph showing antibodies reactive to EmmL protein in mice vaccinated with emmL mRNA or water (controls) (C2) after weeks 1, 2, 3 and 4.

Blood samples from mice vaccinated with either emmL mRNA (treatment) or sterile water (control) were tested for the presence of antibodies that react to emmL protein. As shown in FIG. 9, the blood sample from the control mice (C2) did not contain α-M-like Protein antibodies, whereas the treatment mice (T2) sample showed a slight elevation.

Example 21

Chart 5 shows the results from an experiment in which mice were transplanted with melanoma tumor cells and subsequently injected with either emmL mRNA (treatment) or sterile water (control). The injection regimen began 10 days after tumor implantation. The regimen consisted of three injections, of either treatment or control, administered every seven days. All five mice in the experiment lived past injection #2. At this time, two out of three treatment mice had smaller tumors than the control mice. Three of the five mice survived past injection #3, at which point the two remaining treatment mice tumors were still smaller than the remaining control mouse tumor.

CHART 5

| | Tumor Measurements ($mm^2$) | |
|---|---|---|
| | Post Injection #2 | Post Injection #3 |
| | Treatment | |
| 1 | 44 | 163 |
| 2 | 102 | 100 |
| 3 | 235 | n/a |
| | Control | |
| 1 | 115 | 193 |
| 2 | 188 | n/a |

Example 22

Figure 10:
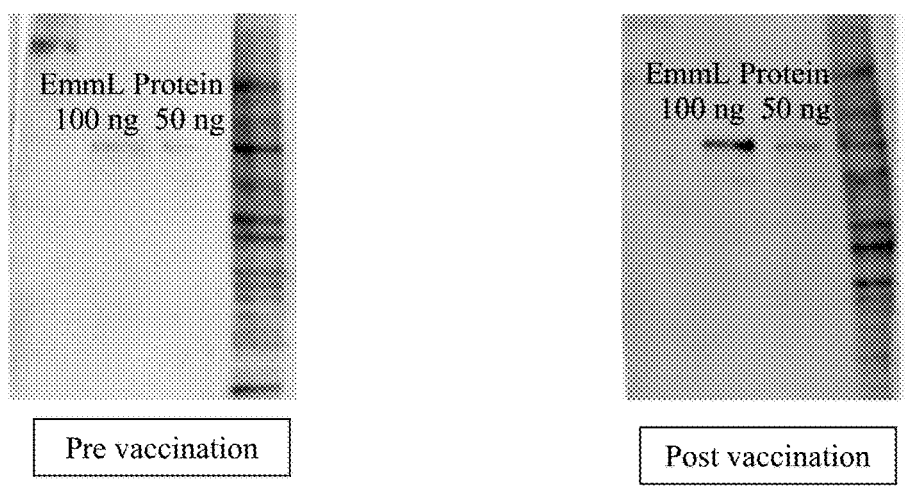
FIG. 10 is a Western blot showing presence of antibodies in mice blood that react to EmmL protein pre and post vaccination with emmL mRNA.

FIG. 10 shows results from an experiment in which blood samples from mice, pre and post vaccination with emmL mRNA, were tested for the presence of antibodies that react to emmL protein. The Western blot images indicate that the blood samples taken post-vaccination have increased binding of antibodies from the pre-vaccination sample.

Example 23

A PCR with high fidelity Taq DNA polymerase is used to amplify the emmL coding region from the pAc/emm55 plasmid. In one embodiment, this amplimer is designed with proximal elements that include restriction endonuclease sites compatible with the pSF-CMV_T7 vector to minimize potentially inhibitory elements within the 5' and 3' UTRs of pSFCMVT7/emmL.

The proximal design elements include restriction endonuclease recognition sites for NcoI and XhoI, an optimal translation initiation sequence (SEQ ID NO: 4 or 5) and two additional stop codons (SEQ ID NO: 6) downstream of the emmL coding region, with respect to the activity of T7 RNA polymerase. The resultant amplimer can be inserted into a PCR cloning vector such as pCR®II-TOPO. The resultant plasmid can be used to transform *E. coli*, select for positive transformation on an agar plates containing a selective antibiotic that matches the PCR cloning vector, such as agar plates containing Luria Bertani broth supplemented with 50-100 μg/mL kanamycin or carbenicillin in the case of pCR®II-TOPO.

Bacterial cultures containing the resultant plasmid can expanded by growth in a liquid antibiotic selective media, such as Luria Bertani broth supplemented with 50-100 μg/mL kanamycin or carbenicillin in the case of pCR®II-TOPO. Plasmid DNA can be prepared from these bacterial cultures using methods known to a person practiced in the art. The restriction endonucleases NcoI and XhoI can then be used to excise the emmL coding region flanked by proximal design elements from pCR®II-TOPO plasmid DNA. The emmL coding region flanked by proximal design elements DNA fragment can then be inserted into the pSF-CMV_T7 vector, which has been digested with NcoI and XhoI. After ligation, bacterial transformation, selection for positive transformation on an agar plates containing 50-100 μg/mL kanamycin, expansion in Luria Bertani broth supplemented with 50-100 μg/mL kanamycin and plasmid DNA preparation using methods known to a person practiced in the art, the resultant plasmid, pSF/emmL can be used as a template for in vitro mRNA synthesis following linearization with the restriction endonuclease XhoI. The resultant mRNA and predicted amino acid sequences are shown as SEQ ID NOs: 13 and 14, respectively.

Example 24

High fidelity Taq DNA polymerase is used to amplify the emmL coding region from the pAc/emm55 plasmid with proximal design elements that include restriction endonuclease sites compatible with the polylinker region of pT7XLUTR. In one embodiment, this can also include an optimal translation initiation sequence (SEQ ID NO: 4 or 5) and two additional stop codons (SEQ ID NO: 6). The full sequence of this embodiment is shown in SEQ ID 15. The resulting amplimer can be inserted into a PCR cloning vector such as pCR®II-TOPO. Following bacterial transformation, selection, expansion and plasmid DNA preparation described in example 23, the resultant plasmid can be digested with restriction endonucleases SacI and SpeI to excise the emmL coding region with proximal design elements from pCR®II-TOPO. The emmL coding region with proximal design elements can then be ligated into the pT7XLUTR plasmid vector that has been digested with SacI and SpeI to generate pT7XLUTR/emmL. The resultant pT7XLUTR/emmL plasmid can be used to transform *E. coli.*

Following selection, expansion and plasmid DNA preparation described in example 23, the resultant pT7XLUTR/emmL plasmid can be used as a template for in vitro mRNA synthesis following linearization with the restriction endonuclease BamHI. The resultant mRNA and predicted amino acid sequences are shown as SEQ ID NOs: 15 and 14, respectively.

Example 25

High fidelity Taq DNA polymerase is used to amplify the emmL coding region from the pAc/emm55 plasmid with minimal 5' and 3' UTRs. The T7 RNA polymerase promoter sequence (SEQ. ID NO 8) is added as a proximal design element along with an optimal translation initiation sequence (SEQ ID NO: 4 or 5), two additional stop codons (SEQ ID NO: 6) and an XhoI restriction endonuclease site.

The resultant PCR product can be inserted into a PCR cloning vector such as pCR®II-TOPO. Following bacterial transformation, selection, expansion and plasmid DNA preparation described in example 23, the resultant plasmid, pT7/emmL can be used as a template for in vitro mRNA synthesis following linearization with the restriction endonuclease XhoI. The resultant mRNA and predicted amino acid sequences are shown as SEQ ID NOs: 16 and 14, respectively.

In examples 23-25, mRNA encoding emmL can be produced using an in vitro transcription reaction. Several modifications to the resultant mRNA can be made in this reaction to improve mRNA and EmmL protein stability and translation efficiency, and to reduce mRNA immunogenicity. For example, a modified nucleic acid can be attached to the 5' end of emmL mRNA such as, but not limited to, anti-reverse Cap Analog [ARCA, P1-(5'-(3'-O-methyl)-7-methyl-guanosyl) P3-(5'-(guanosyl))triphosphate)], N1-methyl-guanosine, 2' fluoro-guanosine, 7-deaza-guanosine, inosine, 8-oxo-guanosine, 2-amino-guanosine, LNA-guanosine and 2-azido-guanosine.

In another example, a polyadenylated [poly(A)] tail approximately 50-200 adenosine monophosphates in length can be attached to the 3' end of emmL mRNA or both 5' modified nucleotide cap and poly(A) tail can be added to emmL mRNA.

emmL mRNA can be synthesized with ribonucleotide analogs. Chemical modifications can be made at this stage to further improve translation efficiency and stability. Examples include; 5-methyl-cytidine-5'-triphosphate, pseudouridine-5'-triphosphate, 2-thiouridine-5'triphosphate, and N1-methylpseudouridine-5'-triphosphate.

SEQ ID NO: 4. Degenerate DNA sequence of an optimal translation initiation sequence. R is A or G, Y is C or T, M is A or C and V is A, C or G.

RYMRMVATGGC

SEQ ID NO: 5. DNA sequence of an optimal translation initiation sequence.

ATAGCCATGGC

SEQ ID NO: 6. DNA sequence containing 2 stop codons. TAATGA

SEQ ID NO: 7. DNA sequence of the restriction endonuclease recognition sites for SacI, NotI, BglII, EcoRV and SpeI.

GAGCTCGCGGCCGCAGATCTGATATCACTAGT

SEQ ID NO: 8. DNA sequence of the T7 RNA polymerase promoter.

TAATACGACTCACTATAG

SEQ ID NO: 9. 50 ribonucleotides of the *Xenopus laevis* beta globin gene 5' untranslated region.

aagcuucuuguucuuuuugcagaagcucagaauaaacgcucaacuuuggc

SEQ ID NO: 10. 74 ribonucleotides of the *Xenopus laevis* beta globin gene 3' untranslated region.

cuuuuugaugccauugccgacgcccuuggcaaggguuaccacuaaaccag
ccucaagaacacccgaauggaguc

SEQ ID NO: 11. DNA sequence of the restriction endonuclease recognition sites for BamHI, EcoRI and XbaI.
GGATCCGAATTCTCTAGA SEQ ID NO: 12. DNA sequence of the synthetic double stranded DNA molecule used to prepare pT7XLUTR. T7 RNA polymerase, restriction endonuclease recognition sites for SacI, NotI, BglII, EcoRV, SpeI, as well as BamHI, EcoRI and XbaI are underlined.

<u>TAATACGACTCACTATAG</u>AAGCTTCTTGTTCTTTTTGCAGAAGCTCAGAA

TAAACGCTCAACTTTGGC<u>GAGCTCGCGGCCGCAGATCTGATATCACTAGT</u>

CTTTTTGATGCCATTGCCGACGCCCTTGGCAAGGGTTACCACTAAACCAG

CCTCAAGAACACCCGAATGGAGT<u>CGGATCCG</u>AATTCTCTAGA

SEQ ID NO: 13 (RNA sequence of example 23). Synthetic mRNA sequence following in vitro mRNA synthesis of emmL from a plasmid template, written from 5' to 3' with respect to the mRNA molecule. An anti-reverse cap analog (ARCA) is added to the 5' end of the transcript and approximately 50-200 adenosine monophosphates ($a^{50-200}$) are added to the 3' end of the transcript during in vitro transcription. 5' lowercase letters are the 5' untranslated region (UTR) from the pSF-T7_CMV plasmid vector. The guanine (g) immediately after the ARCA cap is the +1 ribonucleotide produced by T7 RNA polymerase. Bold indicates ribonucleotides added to make the 5' NcoI restriction endonuclease site, which is underlined, and an optimal translation initiation sequence. Uppercase letters indicate the coding sequence of emmL. At the 3' end of the mRNA sequence, bold indicates two additional stop codons. The 3' XhoI restriction endonuclease site is underlined.

gggagaagaucuuugucgauccuaccauccacucgacacacccgccagcg
gccgcugccaagcuuccgagcucaagcuucgaauucugcagucgacggua
ccgcgggcccgggauccauaaggagcauaaaaauagccAUGGCUAAAAAU
ACCACGAAUAGACACUAUUCGCUUAGAAAAUUAAAAACAGGAACGGCUUC AGUAGCAGUAGCUUUGACUGUUUUAGGGACAGGACUGGUAGCAGGGCAGA
CAGUAAAAGCAAGCCAAACAGAACCAUCUCAGACCAAUAACAGAUUAUAU
CAAGAAAGACAACGUUUACAGGAUUUAAAAAGUAAGUUUCAAGACCUGAA
AAAUCGUUCAGAGGGAUACAUUCAGCAAUACUACGACGAAGAAAAGAACA
GUGGAAGUAACUCUAACUGGUACGCAACCUACUUAAAAGAAUUAAAUGAC
GAAUUUGAACAAGCUUAUAAUGAACUUAGUGGUGAUGGUGUAAAAAAAUU
AGCUGCAAGUUUGAUGGAAGAAAGAGUCGCUUUAAGAGACGAAAUCGAUC
AGAUUAAGAAAAUAUCAGAAGAAUUAAAAAAUAAGCUGAGAGCAAAAGAA
GAAGAAUUAAAAAAUAAAAAAGAGGAACGUGAGCUUGAGCAUGCUGCCUA
UGCAGCAGAUGCAAAGAAACAUGAAGAAUAUGUCAAAUCCAUGUCUCUCG
UACUAAUGGAUAAAGAAGAGGAGCGUCAUAAACUAGAGCAAUCAUUAGAC
ACGGCUAAAGCUGAGCUUGUUAAAAAAGAGCAAGAGUUACAGUUAGUCAA
AGGCAAUCUAGAUCAAAAAGAAAAAGAACUAGAAAAUGAAGAGCUAGCGA
AAGAAAGUGCUAUUAGUGAUUUGACUGAGCAGAUUACUGCUAAGAAGGCU
GAAGUAGAAAAAUUAACUCAAGAUUUAGCUGCUAAGUCUGCUGAAAUUCA
GGAAAAAGAAGCUGAAAAAGAUCGCCAACAGCAUAUGUACGAAGCGUUUA
UGAGCCAGUACAAAGAAAAAGUUGAGAAACAAGAGCAAGAGCUUGCUAAG
CUAAAACAACUUGAAACCAUCAACAACAAUCUAUUAGGUAAUGCUAAGGA
UAUGAUAGCUAAGUUGUCUGCUGAAAAUGAACAAUUAGCAAGCGACAAAG
CAAAACUUGAAGAACAAAACAAGAUUUCAGAAGCGAGCCGUAAAGGUCUU
CGUCGUGACUUGGACGCAUCACGUGAAGCUAAGAAACAAGUUGAAAAAGA
UUUAGCAAACUUGACUGCUGAACUUGAUAAGGUUAAAGAAGAUAAACAAA
UUUCAGACGCAAGCCGUAAAGGUCUUCGUCGUGACUUGGACGCAUCACGU
GAAGCUAAGAAACAAGUUGAAAAAGCUUUAGAAGAAGCAAACAGCAAAUU
AGCGGCUCUUGAAAAACUUAACAAAGAGCUUGAAGAAGCAAGAAAUUAA
CAGAAAAAGAAAAAGCUGAGCUACAAGCGAACUUGAAGCAGAAGCAAAAG
CACUCAAAGAACAAUUAGCGAAACAAGCUGAAGAACUUGCAAAACUAAGA
GCUGGAAAAGCAUCAGACUCACAAACCCCUGAUGCAAAACCAGGAAACAA
AGUUGUUCCAGGUACAGGUCAAGCACCACAAGCAGGCACAAAACCUAACC
AAAACAAAGCACCAAUGAAGGAAACUAAGAGACAGUUACCAUCAACAGGU
GAAGCAGCUAAUCCAUUCUUUACAGCGGCAGCCCUUACUGUUAUGGCAAC
AGCUGGAGUAGCAGCAGUUGUAAAACGCAAAGAAGAAAACGAAGCUGAAU
UCUGCAGAUAUCCAUCACACUGGCGGCCGCGACUCUAGuaauga<u>cucgag</u>

($a^{50-200}$)

SEQ ID NO: 14 (Predicted protein sequence of examples 23-25). One letter predicted amino acid sequence of emmL transcripts produced in examples 2-4. * indicates stop codon.

MAKNTTNRHYSLRKLKTGTASVAVALTVLGTGLVAGQTVKASQTEPSQTN
NRLYQERQRLQDLKSKFQDLKNRSEGYIQQYYDEEKNSGSNSNWYATYLK
ELNDEFEQAYNELSGDGVKKLAASLMEERVALRDEIDQIKKISEELKNKL

RAKEEELKNKKEERELEHAAYAADAKKHEEYVKSMSLVLMDKEEERHKLE

QSLDTAKAELVKKEQELQLVKGNLDQKEKELENEELAKESAISDLTEQIT

AKKAEVEKLTQDLAAKSAEIQEKEAEKDRQQHMYEAFMSQYKEKVEKQEQ

ELAKLKQLETINNNLLGNAKDMIAKLSAENEQLASDKAKLEEQNKISEAS

RKGLRRDLDASREAKKQVEKDLANLTAELDKVKEDKQISDASRKGLRRDL

DASREAKKQVEKALEEANSKLAALEKLNKELEESKKLTEKEKAELQAKLE

AEAKALKEQLAKQAEELAKLRAGKASDSQTPDAKPGNKVVPGTGQAPQAG

TKPNQNKAPMKETKRQLPSTGEAANPFFTAAALTVMATAGVAAVVKRKEE

NEAEFCRYPSHWRPRL*

SEQ ID NO: 15 (RNA sequence of example 24). Synthetic mRNA sequence following in vitro mRNA synthesis of emmL from the pT7XLURT plasmid template linearized with restriction endonuclease BamHI, written from 5' to 3' with respect to the mRNA molecule. An anti-reverse cap analog (ARCA) is added to the 5' end of the transcript and approximately 50-200 adenosine monophosphates ($a^{50-200}$) are added to the 3' end of the transcript during in vitro transcription. The guanine (g) immediately after the ARCA cap is the +1 ribonucleotide produced by T7 RNA polymerase. 5' lowercase letters are from the 5' untranslated region of the *Xenopus laevis* beta globin gene. Bold indicates ribonucleotides added to make an optimal translation initiation sequence. A SacI restriction endonuclease site 5' of the emmL coding region is underlined. Uppercase letters indicate the coding sequence of emmL. Lowercase letters 3' of the coding region are the 3' untranslated region of the *Xenopus laevis* beta globin gene. At the 3' end of the mRNA sequence, bold indicates two additional stop codons. SpeI and BamHI restriction endonuclease sites are underlined.

gaagcuucuuguucuuuuugcagaagcucagaauaaacgcucaacuuugg c<u>gagcuc</u>auagccAUGGCUAAAAAUACCACGAAUAGACACUAUUCGCUUA

GAAAAUUAAAAACAGGAACGGCUUCAGUAGCAGUAGCUUUGACUGUUUUA

GGGACAGGACUGGUAGCAGGGCAGACAGUAAAAGCAAGCCAAACAGAACC

AUCUCAGACCAAUAACAGAUUAUAUCAAGAAAGACAACGUUUACAGGAUU

UAAAAAGUAAGUUUCAAGACCUGAAAAAUCGUUCAGAGGGAUACAUUCAG

CAAUACUACGACGAAGAAAGAACAGUGGAAGUAACUCUAACUGGUACGC

AACCUACUUAAAAGAAUUAAAUGACGAAUUUGAACAAGCUUAUAAUGAAC

UUAGUGGUGAUGGUGUAAAAAAAUUAGCUGCAAGUUUGAUGGAAGAAAGA

GUCGCUUUAAGAGACGAAAUCGAUCAGAUUAAGAAAAAUAUCAGAAGAAUU

AAAAAAUAAGCUGAGAGCAAAAGAAGAAGAAUUAAAAAAUAAAAAAGAGG

AACGUGAGCUUGAGCAUGCUGCCUAUGCAGCAGAUGCAAAGAAACAUGAA

GAAUAUGUCAAAUCCAUGUCUCUCGUACUAAUGGAUAAAGAAGAGGAGCG

UCAUAAACUAGAGCAAUCAUUAGACACGGCUAAAGCUGAGCUUGUUAAAA

AAGAGCAAGAGUUACAGUUAGUCAAAGGCAAUCUAGAUCAAAAAGAAAAA

GAACUAGAAAAUGAAGAGCUAGCGAAAGAAAGUGCUAUUAGUGAUUUGAC

UGAGCAGAUUACUGCUAAGAAGGCUGAAGUAGAAAAAUUAACUCAAGAUU

UAGCUGCUAAGUCUGCUGAAAUUCAGGAAAAAGAAGCUGAAAAAGAUCGC

CAACAGCAUAUGUACGAAGCGUUUAUGAGCCAGUACAAAGAAAAAGUUGA

GAAACAAGAGCAAGAGCUUGCUAAGCUAAAACAACUUGAAACCAUCAACA

ACAAUCUAUUAGGUAAUGCUAAGGAUAUGAUAGCUAAGUUGUCUGCUGAA

AAUGAACAAUUAGCAAGCGACAAAGCAAAACUUGAAGAACAAAACAAGAU

UUCAGAAGCGAGCCGUAAAGGUCUUCGUCGUGACUUGGACGCAUCACGUG

AAGCUAAGAAACAAGUUGAAAAAGAUUUAGCAAACUUGACUGCUGAACUU

GAUAAGGUUAAAGAAGAUAAACAAAUUUCAGACGCAAGCCGUAAAGGUCU

UCGUCGUGACUUGGACGCAUCACGUGAAGCUAAGAAACAAGUUGAAAAAG

CUUUAGAAGAAGCAAACAGCAAAUUAGCGGCUCUUGAAAAACUUAACAAA

GAGCUUGAAGAAAGCAAGAAAUUAACAGAAAAAGAAAAAGCUGAGCUACA

AGCGAAACUUGAAGCAGAAGCAAAAGCACUCAAAGAACAAUUAGCGAAAC

AAGCUGAAGAACUUGCAAAACUAAGAGCUGGAAAAGCAUCAGACUCACAA

ACCCCUGAUGCAAAACCAGGAAACAAAGUUGUUCCAGGUACAGGUCAAGC

ACCACAAGCAGGCACAAAACCUAACCAAAACAAAGCACCAAUGAAGGAAA

CUAAGAGACAGUUACCAUCAACAGGUGAAGCAGCUAAUCCAUUCUUUACA

GCGGCAGCCCUUACUGUUAUGGCAACAGCUGGAGUAGCAGCAGUUGUAAA

ACGCAAAGAAGAAAACGAAGCUGAAUUCUGCAGAUAUCCAUCACACUGGC

GGCCGCGACUCUAGuaauga<u>acuagu</u>cuuuuugaugccauugccgacgcc cuuggcaagggguuaccacuaaaccagccucaagaacacccgaaugga<u>guc ggaucc</u> ($a^{50-200}$)

SEQ ID NO: 16 (RNA sequence of example 24). Synthetic mRNA sequence following in vitro mRNA synthesis of emmL from a plasmid template, written from 5' to 3' with respect to the mRNA molecule. An anti-reverse cap analog (ARCA) is added to the 5' end of the transcript and approximately 50-200 adenosine monophosphates ($a^{50-200}$) are added to the 3' end of the transcript during in vitro transcription. The guanine (g) immediately after the ARCA cap is the +1 ribonucleotide produced by T7 RNA polymerase. Bold indicates ribonucleotides added to make an optimal translation initiation sequence. Uppercase letters indicate the coding sequence of emmL. At the 3' end of the mRNA sequence, bold indicates two additional stop codons. The 3' XhoI site is underlined.

gauagccAUGGCUAAAAAUACCACGAAUAGACACUAUUCGCUUAGAAAAU

UAAAAACAGGAACGGCUUCAGUAGCAGUAGCUUUGACUGUUUUAGGGACA

GGACUGGUAGCAGGGCAGACAGUAAAAGCAAGCCAAACAGAACCAUCUCA

GACCAAUAACAGAUUAUAUCAAGAAAGACAACGUUUACAGGAUUUAAAAA

GUAAGUUUCAAGACCUGAAAAAUCGUUCAGAGGGAUACAUUCAGCAAUAC

UACGACGAAGAAAGAACAGUGGAAGUAACUCUAACUGGUACGCAACCUA

CUUAAAAGAAUUAAAUGACGAAUUUGAACAAGCUUAUAAUGAACUUAGUG

GUGAUGGUGUAAAAAAAUUAGCUGCAAGUUUGAUGGAAGAAAGAGUCGCU

UUAAGAGACGAAAUCGAUCAGAUUAAGAAAAAUAUCAGAAGAAUUAAAAA

UAAGCUGAGAGCAAAAGAAGAAGAAUUAAAAAAUAAAAAAGAGGAACGUG

-continued

AGCUUGAGCAUGCUGCCUAUGCAGCAGAUGCAAAGAAACAUGAAGAAUAU
GUCAAAUCCAUGUCUCUCGUACUAAUGGAUAAAGAAGAGGAGCGUCAUAA
ACUAGAGCAAUCAUUAGACACGGCUAAAGCUGAGCUUGUUAAAAAGAGC
AAGAGUUACAGUUAGUCAAAGGCAAUCUAGAUCAAAAAGAAAAAGAACUA
GAAAAUGAAGAGCUAGCGAAAGAAAGUGCUAUUAGUGAUUUGACUGAGCA
GAUUACUGCUAAGAAGGCUGAAGUAGAAAAAUUAACUCAAGAUUUAGCUG
CUAAGUCUGCUGAAAUUCAGGAAAAAGAAGCUGAAAAAGAUCGCCAACAG
CAUAUGUACGAAGCGUUUAUGAGCCAGUACAAAGAAAAAGUUGAGAAACA
AGAGCAAGAGCUUGCUAAGCUAAAACAACUUGAAACCAUCAACAACAAUC
UAUUAGGUAAUGCUAAGGAUAUGAUAGCUAAGUUGUCUGCUGAAAAUGAA
CAAUUAGCAAGCGACAAAGCAAAACUUGAAGAACAAAACAAGAUUUCAGA
AGCGAGCCGUAAAGGUCUUCGUCGUGACUUGGACGCAUCACGUGAAGCUA
AGAAACAAGUUGAAAAAGAUUUAGCAAACUUGACUGCUGAACUUGAUAAG

-continued

GUUAAAGAAGAUAAACAAAUUUCAGACGCAAGCCGUAAAGGUCUUCGUCG
UGACUUGGACGCAUCACGUGAAGCUAAGAAACAAGUUGAAAAAGCUUUAG
AAGAAGCAAACAGCAAAUUAGCGGCUCUUGAAAAACUUAACAAAGAGCUU
GAAGAAAGCAAGAAAUUAACAGAAAAAGAAAAAGCUGAGCUACAAGCGAA
ACUUGAAGCAGAAGCAAAAGCACUCAAAGAACAAUUAGCGAAACAAGCUG
AAGAACUUGCAAAACUAAGAGCUGGAAAAGCAUCAGACUCACAAACCCCU
GAUGCAAAACCAGGAAACAAAGUUGUUCCAGGUACAGGUCAAGCACCACA
AGCAGGCACAAAACCUAACCAAAACAAAGCACCAAUGAAGGAAACUAAGA
GACAGUUACCAUCAACAGGUGAAGCAGCUAAUCCAUUCUUUACAGCGGCA
GCCCUUACUGUUAUGGCAACAGCUGGAGUAGCAGCAGUUGUAAAACGCAA
AGAAGAAAACGAAGCUGAAUUCUGCAGAUAUCCAUCACACUGGCGGCCGC
GACUCUAGuaaugacucgag(a⁵⁰⁻²⁰⁰)

We claim:

1. A ribonucleic acid comprising the sequence of SEQ ID NO: 1, wherein said ribonucleic acid expresses an immunogenic polypeptide in tumor cells transfected with said ribonucleic acid.

2. A vaccine composition in a pharmaceutically acceptable excipient comprising a nucleic acid having SEQ ID NO: 1, wherein an immunogenic response is produced when the vaccine composition is administered to a cancer patient.

3. A cancer cell vaccine composition comprising tumor cells transformed with a ribonucleic acid having the sequence of SEQ ID NO: 1.

4. A vaccine composition comprising tumor cells transfected in vitro with a synthetic ribonucleic acid having the sequence of SEQ ID NO: 1 comprised in a pharmaceutically acceptable carrier.

5. The vaccine composition of claim 4, wherein the synthetic ribonucleic acid expresses an antigenic protein.

6. The vaccine composition of claim 4, wherein the transfected tumor cells are tumor cells isolated from a cancer patient.

7. The vaccine composition of claim 6, wherein the tumor cells are selected from carcinoma, sarcoma, myeloma, lymphoma or leukemia.

8. The vaccine composition of claim 2, wherein the pharmaceutically acceptable excipient is nuclease free aqueous medium.

* * * * *

SEQUENCE LISTING

<160> NUMBER OF SEQ ID NOS: 16

<210> SEQ ID NO 1
<211> LENGTH: 1854
<212> TYPE: RNA
<213> ORGANISM: Artificial Sequence
<220> FEATURE:
<223> OTHER INFORMATION: Theoretical emm55 mRNA sequence
<220> FEATURE:
<221> NAME/KEY: misc_feature
<222> LOCATION: (1)..(2)
<223> OTHER INFORMATION: 5' ARCA methylguanosine cap
<220> FEATURE:
<221> NAME/KEY: misc_feature
<222> LOCATION: (3)..(132)
<223> OTHER INFORMATION: 5' untranslated region
<220> FEATURE:
<221> NAME/KEY: misc_feature
<222> LOCATION: (133)..(135)
<223> OTHER INFORMATION: start codon
<220> FEATURE:
<221> NAME/KEY: misc_feature
<222> LOCATION: (133)..(1804)
<223> OTHER INFORMATION: emm55 gene
<220> FEATURE:
<221> NAME/KEY: misc_feature
<222> LOCATION: (1806)..(1854)
<223> OTHER INFORMATION: Poly(A) tail, minimum of 50 adenosines

<400> SEQUENCE: 1
gggagaagau cuuugucgau ccuaccaucc acucgacaca cccgccagcg gccgcugcca      60
agcuuccgag cucaagcuuc gaauucugca gucgacggua ccgcgggccc gggauccaua     120
aggagcauaa aaauggcuaa aaauaccacg aaugacacu auucgcuuag aaaauuaaaa     180
acaggaacgg cuucaguagc aguagcuuug acuguuuuag ggacaggacu gguagcaggg     240
cagacaguaa aagcaagcca aacagaacca ucucagacca auaacagauu auaucaagaa     300
agacaacguu uacaggauuu aaaaaguaag uuucaagacc ugaaaaaucg uucagaggga     360
uacauucagc aauacuacga cgaagaaaag aacaguggaa guaacucuaa cugguacgca     420
accuacuuaa aagaauuaaa ugacgaauuu gaacaagcuu auaaugaacu aguggugau     480 ggguguaaaaa aauuagcugc aaguuugaug gaagaaagag ucgcuuuaag agacgaaauc     540

-continued

| | |
|---|---|
| gaucagauua agaaaauauc agaagaauua aaaaauaagc ugagagcaaa agaagaagaa | 600 |
| uuaaaaaaua aaaagagga acgugagcuu gagcaugcug ccuaugcagc agaugcaaag | 660 |
| aaacaugaag aauaugucaa auccaugucu cucguacuaa uggauaaaga agaggagcgu | 720 |
| cauaaacuag agcaaucauu agacacggcu aaagcugagc uuguuaaaaa agagcaagag | 780 |
| uuacaguuag ucaaaggcaa ucuagaucaa aagaaaaag aacuagaaaa ugaagagcua | 840 |
| gcgaaagaaa gugcuauuag ugauuugacu gagcagauua cugcuaagaa ggcugaagua | 900 |
| gaaaaauuaa cucaagauuu agcugcuaag ucugcugaaa uucaggaaaa agaagcugaa | 960 |
| aaagaucgcc aacagcauau guacgaagcg uuuaugagcc aguacaaaga aaaaguugag | 1020 |
| aaacaagagc aagagcuugc uaagcuaaaa caacuugaaa ccaucaacaa caaucuauua | 1080 |
| gguaaugcua aggauaugau agcuaaguug cugcugaaa augaacaauu agcaagcgac | 1140 |
| aaagcaaaac uugaagaaca aaacaagauu ucagaagcga gccguaaagg ucuucgucgu | 1200 |
| gacuuggacg caucacguga agcuaagaaa caaguugaaa aagauuuagc aaacuugacu | 1260 |
| gcugaacuug auaagguuaa agaagauaaa caaauuucag acgcaagccg uaaaggucuu | 1320 |
| cgucgugacu uggacgcauc acgugaagcu aagaaacaag uugaaaaagc uuuagaagaa | 1380 |
| gcaaacagca aauuagcggc ucuugaaaaa cuuaacaaag agcuugaaga aagcaagaaa | 1440 |
| uuaacagaaa aagaaaaagc ugagcuacaa gcgaaacuug aagcagaagc aaaagcacuc | 1500 |
| aaagaacaau uagcgaaaca agcugaagaa cuugcaaaac uaagagcugg aaaagcauca | 1560 |
| gacucacaaa ccccugaugc aaaaccagga aacaaaguug uuccagguac aggucaagca | 1620 |
| ccacaagcag gcacaaaacc uaaccaaaac aaagcaccaa ugaaggaaac uaagagacag | 1680 |
| uuaccaucaa caggugaagc agcuaauucca uucuuuacag cggcagcccu uacuguuaug | 1740 |
| gcaacagcug gaguagcagc aguuguaaaa cgcaaagaag aaaacgaagc ugaauucugc | 1800 |
| agauaaaaaa aaaaaaaaa aaaaaaaaaa aaaaaaaaaa aaaaaaaaaa aaaa | 1854 |

<210> SEQ ID NO 2
<211> LENGTH: 557
<212> TYPE: PRT
<213> ORGANISM: Artificial Sequence
<220> FEATURE:
<223> OTHER INFORMATION: Emm55 Protein Sequence

<400> SEQUENCE: 2

Met Ala Lys Asn Thr Thr Asn Arg His Tyr Ser Leu Arg Lys Leu Lys
1               5                   10                  15

Thr Gly Thr Ala Ser Val Ala Val Ala Leu Thr Val Leu Gly Thr Gly
            20                  25                  30

Leu Val Ala Gly Gln Thr Val Lys Ala Ser Gln Thr Glu Pro Ser Gln
        35                  40                  45

Thr Asn Asn Arg Leu Tyr Gln Glu Arg Gln Arg Leu Gln Asp Leu Lys
    50                  55                  60

Ser Lys Phe Gln Asp Leu Lys Asn Arg Ser Glu Gly Tyr Ile Gln Gln
65                  70                  75                  80

Tyr Tyr Asp Glu Glu Lys Asn Ser Gly Ser Asn Ser Asn Trp Tyr Ala
                85                  90                  95

Thr Tyr Leu Lys Glu Leu Asn Asp Glu Phe Glu Gln Ala Tyr Asn Glu
            100                 105                 110

Leu Ser Gly Asp Gly Val Lys Lys Leu Ala Ala Ser Leu Met Glu Glu
        115                 120                 125

Arg Val Ala Leu Arg Asp Glu Ile Asp Gln Ile Lys Lys Ile Ser Glu

```
            130                 135                 140
Glu Leu Lys Asn Lys Leu Arg Ala Lys Glu Glu Leu Lys Asn Lys
145                 150                 155                 160

Lys Glu Glu Arg Glu Leu Glu His Ala Ala Tyr Ala Ala Asp Ala Lys
                    165                 170                 175

Lys His Glu Glu Tyr Val Lys Ser Met Ser Leu Val Leu Met Asp Lys
                180                 185                 190

Glu Glu Glu Arg His Lys Leu Glu Gln Ser Leu Asp Thr Ala Lys Ala
                195                 200                 205

Glu Leu Val Lys Lys Glu Gln Glu Leu Gln Leu Val Lys Gly Asn Leu
                210                 215                 220

Asp Gln Lys Glu Lys Glu Leu Glu Asn Glu Glu Leu Ala Lys Glu Ser
225                 230                 235                 240

Ala Ile Ser Asp Leu Thr Glu Gln Ile Thr Ala Lys Lys Ala Glu Val
                245                 250                 255

Glu Lys Leu Thr Gln Asp Leu Ala Ala Lys Ser Ala Glu Ile Gln Glu
                260                 265                 270

Lys Glu Ala Glu Lys Asp Arg Gln Gln His Met Tyr Glu Ala Phe Met
                275                 280                 285

Ser Gln Tyr Lys Glu Lys Val Glu Lys Gln Glu Gln Glu Leu Ala Lys
                290                 295                 300

Leu Lys Gln Leu Glu Thr Ile Asn Asn Asn Leu Leu Gly Asn Ala Lys
305                 310                 315                 320

Asp Met Ile Ala Lys Leu Ser Ala Glu Asn Glu Gln Leu Ala Ser Asp
                325                 330                 335

Lys Ala Lys Leu Glu Glu Gln Asn Lys Ile Ser Glu Ala Ser Arg Lys
                340                 345                 350

Gly Leu Arg Arg Asp Leu Asp Ala Ser Arg Glu Ala Lys Lys Gln Val
                355                 360                 365

Glu Lys Asp Leu Ala Asn Leu Thr Ala Glu Leu Asp Lys Val Lys Glu
                370                 375                 380

Asp Lys Gln Ile Ser Asp Ala Ser Arg Lys Gly Leu Arg Arg Asp Leu
385                 390                 395                 400

Asp Ala Ser Arg Glu Ala Lys Lys Gln Val Glu Lys Ala Leu Glu Glu
                405                 410                 415

Ala Asn Ser Lys Leu Ala Ala Leu Glu Lys Leu Asn Lys Glu Leu Glu
                420                 425                 430

Glu Ser Lys Lys Leu Thr Glu Lys Glu Lys Ala Glu Leu Gln Ala Lys
                435                 440                 445

Leu Glu Ala Glu Ala Lys Ala Leu Lys Glu Gln Leu Ala Lys Gln Ala
                450                 455                 460

Glu Glu Leu Ala Lys Leu Arg Ala Gly Lys Ala Ser Asp Ser Gln Thr
465                 470                 475                 480

Pro Asp Ala Lys Pro Gly Asn Lys Val Val Pro Gly Thr Gly Gln Ala
                485                 490                 495

Pro Gln Ala Gly Thr Lys Pro Asn Gln Asn Lys Ala Pro Met Lys Glu
                500                 505                 510

Thr Lys Arg Gln Leu Pro Ser Thr Gly Glu Ala Ala Asn Pro Phe Phe
                515                 520                 525

Thr Ala Ala Ala Leu Thr Val Met Ala Thr Gly Val Ala Ala Val
                530                 535                 540

Val Lys Arg Lys Glu Glu Asn Glu Ala Glu Phe Cys Arg
545                 550                 555
```

<210> SEQ ID NO 3
<211> LENGTH: 179
<212> TYPE: RNA
<213> ORGANISM: Artificial Sequence
<220> FEATURE:
<223> OTHER INFORMATION: Theoretical untranslated mRNA sequence of SEQ
      ID NO: 1
<220> FEATURE:
<221> NAME/KEY: misc_feature
<222> LOCATION: (1)..(2)
<223> OTHER INFORMATION: 5' ARCA methylguanosine cap
<220> FEATURE:
<221> NAME/KEY: misc_feature
<222> LOCATION: (3)..(132)
<223> OTHER INFORMATION: 5' untranslated region
<220> FEATURE:
<221> NAME/KEY: misc_feature
<222> LOCATION: (133)..(135)
<223> OTHER INFORMATION: start codon
<220> FEATURE:
<221> NAME/KEY: misc_feature
<222> LOCATION: (136)..(179)
<223> OTHER INFORMATION: Poly(A) tail, minimum of 50 adenosines

<400> SEQUENCE: 3
gggagaagau cuuugucgau ccuaccaucc acucgacaca cccgccagcg gccgcugcca      60
agcuuccgag cucaagcuuc gaauucugca gucgacggua ccgcgggccc gggauccaua     120
aggagcauaa aaaugaaaaa aaaaaaaaaa aaaaaaaaaa aaaaaaaaaa aaaaaaaa      179

<210> SEQ ID NO 4
<211> LENGTH: 11
<212> TYPE: DNA
<213> ORGANISM: Artificial Sequence
<220> FEATURE:
<223> OTHER INFORMATION: Degenerate DNA sequence of an optimal
      translation initiation sequence
<220> FEATURE:
<221> NAME/KEY: misc_feature
<222> LOCATION: (1)..(1)
<223> OTHER INFORMATION: R is A or G
<220> FEATURE:
<221> NAME/KEY: misc_feature
<222> LOCATION: (2)..(2)
<223> OTHER INFORMATION: Y is C or T
<220> FEATURE:
<221> NAME/KEY: misc_feature
<222> LOCATION: (3)..(3)
<223> OTHER INFORMATION: M is A or C
<220> FEATURE:
<221> NAME/KEY: misc_feature
<222> LOCATION: (4)..(4)
<223> OTHER INFORMATION: R is A or G
<220> FEATURE:
<221> NAME/KEY: misc_feature
<222> LOCATION: (5)..(5)
<223> OTHER INFORMATION: M is A or C
<220> FEATURE:
<221> NAME/KEY: misc_feature
<222> LOCATION: (6)..(6)
<223> OTHER INFORMATION: V is A , C or G

<400> SEQUENCE: 4
rymrmvatgg c                                                           11

<210> SEQ ID NO 5
<211> LENGTH: 11
<212> TYPE: DNA
<213> ORGANISM: Artificial Sequence
<220> FEATURE:
<223> OTHER INFORMATION: DNA sequence of an optimal translation
      initiation sequence

```
<400> SEQUENCE: 5
atagccatgg c                                                            11

<210> SEQ ID NO 6
<211> LENGTH: 6
<212> TYPE: DNA
<213> ORGANISM: Artificial Sequence
<220> FEATURE:
<223> OTHER INFORMATION: DNA sequence containing 2 stop codons

<400> SEQUENCE: 6 taatga                                                                   6

<210> SEQ ID NO 7
<211> LENGTH: 32
<212> TYPE: DNA
<213> ORGANISM: Artificial Sequence
<220> FEATURE:
<223> OTHER INFORMATION: DNA sequence of the restriction endonuclease
      recognition sites for SacI, NotI, BglII, EcoRV and SpeI

<400> SEQUENCE: 7
gagctcgcgg ccgcagatct gatatcacta gt                                     32

<210> SEQ ID NO 8
<211> LENGTH: 18
<212> TYPE: DNA
<213> ORGANISM: Artificial Sequence
<220> FEATURE:
<223> OTHER INFORMATION: DNA sequence of the T7 RNA polymerase promoter

<400> SEQUENCE: 8
taatacgact cactatag                                                     18

<210> SEQ ID NO 9
<211> LENGTH: 50
<212> TYPE: RNA
<213> ORGANISM: Xenopus laevis
<220> FEATURE:
<221> NAME/KEY: misc_feature
<222> LOCATION: (1)..(50)
<223> OTHER INFORMATION: 5' untranslated region

<400> SEQUENCE: 9
aagcuucuug uucuuuuugc agaagcucag aauaaacgcu caacuuuggc                  50

<210> SEQ ID NO 10
<211> LENGTH: 74
<212> TYPE: RNA
<213> ORGANISM: Xenopus laevis
<220> FEATURE:
<221> NAME/KEY: misc_feature
<222> LOCATION: (1)..(74)
<223> OTHER INFORMATION: 3' untranslated region

<400> SEQUENCE: 10
cuuuuugaug ccauugccga cgcccuuggc aagggguuacc acuaaaccag ccucaagaac       60
acccgaaugg aguc                                                         74

<210> SEQ ID NO 11
<211> LENGTH: 18
<212> TYPE: DNA
<213> ORGANISM: Artificial Sequence
<220> FEATURE:
<223> OTHER INFORMATION: DNA sequence of the restriction endonuclease
``` recognition sites for BamHI, EcoRI and XbaI

<400> SEQUENCE: 11
ggatccgaat tctctaga                                                     18

<210> SEQ ID NO 12
<211> LENGTH: 192
<212> TYPE: DNA
<213> ORGANISM: Artificial Sequence
<220> FEATURE:
<223> OTHER INFORMATION: DNA sequence of the synthetic double stranded
      DNA molecule used to prepare pT7XLUTR

<400> SEQUENCE: 12
taatacgact cactatagaa gcttcttgtt cttttttgcag aagctcagaa taaacgctca       60
actttggcga gctcgcggcc gcagatctga tatcactagt cttttttgatg ccattgccga     120 cgcccttggc aagggttacc actaaaccag cctcaagaac acccgaatgg agtcggatcc     180
gaattctcta ga                                                         192

<210> SEQ ID NO 13
<211> LENGTH: 1851
<212> TYPE: RNA
<213> ORGANISM: Artificial Sequence
<220> FEATURE:
<223> OTHER INFORMATION: Synthetic

<400> SEQUENCE: 13
gggagaagau cuuugucgau ccuaccaucc acucgacaca cccgccagcg gccgcugcca       60
agcuuccgag cucaagcuuc gaauucugca gucgacggua ccgcgggccc gggauccaua     120
aggagcauaa aaauagccau ggcuaaaaau accacgaaua gacacuauuc gcuuagaaaa     180
uuaaaaacag gaacggcuuc aguagcagua gcuuugacug uuuuagggac aggacuggua     240
gcagggcaga caguaaaagc aagccaaaca gaaccaucuc agaccaauaa cagauuauau     300
caagaaagac aacguuuaca ggauuuaaaa aguaaguuuc aagaccugaa aaaucguuca     360
gagggauaca uucagcaaua cuacgacgaa gaaaagaaca guggaaguaa cucuaacugg     420
uacgcaaccu acuuaaaaga auuaaaugac gaauuugaac aagcuuauaa ugaacuuagu     480
ggugauggug uaaaaaaauu agcugcaagu uugauggaag aaagagucgc uuuaagagac     540
gaaaucgauc agauuaagaa aauaucagaa gaauuaaaaa auaagcugag agcaaaagaa     600
gaagaauuaa aaaauaaaaa agaggaacgu gagcuugagc augcugccua ugcagcagau     660
gcaaagaaac augaagaaua ugucaaauuc auguccucg uacuaaugga uaagaagag     720 gagcgucaua aacuagagca aucauuagac acggcuaaag cugagcuugu uaaaaaagag     780
caagaguuac aguagucaa aggcaaucua gaucaaaaag aaaaagaacu agaaaaugaa     840
gagcuagcga agaaagugc uauuagugau uugacugagc agauuacugc uaagaaggcu     900
gaaguagaaa aauuaacuca agauuuagcu gcuaagucug cugaaauuca ggaaaaagaa     960
gcugaaaaag aucgccaaca gcauauguac gaagcguuua ugagccagua caaagaaaaa    1020
guugagaaac aagagcaaga gcuugcuaag cuaaaacaac uugaaaccau caacaacaau    1080
cuauuaggua augcuaagga uaugauagcu aaguugucug cugaaaauga acaauuagca    1140
agcgacaaag caaaacuuga gaacaaaac aagauuucag aagcgagccg uaaaggucuu    1200
cgucgugacu uggacgcauc acgugaagcu aagaaacaag uugaaaaaga uuuagcaaac    1260
uugacugcug aacuugauaa gguuaagaa gauaaacaaa uuucagacgc aagccguaaa    1320

-continued

```
ggucuucguc gugacuugga cgcaucacgu gaagcuaaga acaaguuga aaaagcuuua      1380 gaagaagcaa acagcaaauu agcggcucuu gaaaaacuua acaaagagcu ugaagaaagc      1440
aagaaauuaa cagaaaaaga aaaagcugag cuacaagcga acuugaagc agaagcaaaa       1500 gcacucaaag aacaauuagc gaaacaagcu gaagaacuug caaaacuaag gcuggaaaa       1560 gcaucagacu cacaaacccc ugaugcaaaa ccaggaaaca aaguuguucc agguacaggu      1620
caagcaccac aagcaggcac aaaccuaac caaaacaaag caccaaugaa ggaaacuaag       1680
agacaguuac caucaacagg ugaagcagcu aauccauucu uuacagcggc agcccuuacu      1740
guuauggcaa cagcuggagu agcagcaguu guaaaacgca aagaagaaaa cgaagcugaa      1800
uucugcagau auccaucaca cuggcggccg cgacucuagu aaugacucga g              1851
```

<210> SEQ ID NO 14
<211> LENGTH: 566
<212> TYPE: PRT
<213> ORGANISM: Artificial Sequence
<220> FEATURE:
<223> OTHER INFORMATION: Synthetic

<400> SEQUENCE: 14

```
Met Ala Lys Asn Thr Thr Asn Arg His Tyr Ser Leu Arg Lys Leu Lys
1               5                   10                  15

Thr Gly Thr Ala Ser Val Ala Val Ala Leu Thr Val Leu Gly Thr Gly
            20                  25                  30

Leu Val Ala Gly Gln Thr Val Lys Ala Ser Gln Thr Glu Pro Ser Gln
        35                  40                  45

Thr Asn Asn Arg Leu Tyr Gln Glu Arg Gln Arg Leu Gln Asp Leu Lys
    50                  55                  60

Ser Lys Phe Gln Asp Leu Lys Asn Arg Ser Glu Gly Tyr Ile Gln Gln
65                  70                  75                  80

Tyr Tyr Asp Glu Glu Lys Asn Ser Gly Ser Asn Ser Asn Trp Tyr Ala
                85                  90                  95

Thr Tyr Leu Lys Glu Leu Asn Asp Glu Phe Glu Gln Ala Tyr Asn Glu
            100                 105                 110

Leu Ser Gly Asp Gly Val Lys Lys Leu Ala Ala Ser Leu Met Glu Glu
        115                 120                 125

Arg Val Ala Leu Arg Asp Glu Ile Asp Gln Ile Lys Lys Ile Ser Glu
    130                 135                 140

Glu Leu Lys Asn Lys Leu Arg Ala Lys Glu Glu Leu Lys Asn Lys
145                 150                 155                 160

Lys Glu Glu Arg Glu Leu Glu His Ala Ala Tyr Ala Ala Asp Ala Lys
                165                 170                 175

Lys His Glu Glu Tyr Val Lys Ser Met Ser Leu Val Leu Met Asp Lys
            180                 185                 190

Glu Glu Glu Arg His Lys Leu Glu Gln Ser Leu Asp Thr Ala Lys Ala
        195                 200                 205

Glu Leu Val Lys Lys Glu Gln Glu Leu Gln Leu Val Lys Gly Asn Leu
    210                 215                 220

Asp Gln Lys Glu Lys Glu Leu Glu Asn Glu Glu Leu Ala Lys Glu Ser
225                 230                 235                 240

Ala Ile Ser Asp Leu Thr Glu Gln Ile Thr Ala Lys Lys Ala Glu Val
                245                 250                 255

Glu Lys Leu Thr Gln Asp Leu Ala Ala Lys Ser Ala Glu Ile Gln Glu
            260                 265                 270
```

-continued

```
Lys Glu Ala Glu Lys Asp Arg Gln Gln His Met Tyr Glu Ala Phe Met
            275                 280                 285
Ser Gln Tyr Lys Glu Lys Val Glu Lys Gln Gln Glu Leu Ala Lys
    290                 295                 300
Leu Lys Gln Leu Glu Thr Ile Asn Asn Asn Leu Leu Gly Asn Ala Lys
305                 310                 315                 320
Asp Met Ile Ala Lys Leu Ser Ala Glu Asn Glu Gln Leu Ala Ser Asp
                325                 330                 335
Lys Ala Lys Leu Glu Glu Gln Asn Lys Ile Ser Glu Ala Ser Arg Lys
            340                 345                 350
Gly Leu Arg Arg Asp Leu Asp Ala Ser Arg Glu Ala Lys Lys Gln Val
        355                 360                 365
Glu Lys Asp Leu Ala Asn Leu Thr Ala Glu Leu Asp Lys Val Lys Glu
    370                 375                 380
Asp Lys Gln Ile Ser Asp Ala Ser Arg Lys Gly Leu Arg Arg Asp Leu
385                 390                 395                 400
Asp Ala Ser Arg Glu Ala Lys Lys Gln Val Glu Lys Ala Leu Glu Glu
                405                 410                 415
Ala Asn Ser Lys Leu Ala Ala Leu Glu Lys Leu Asn Lys Glu Leu Glu
            420                 425                 430
Glu Ser Lys Lys Leu Thr Glu Lys Glu Lys Ala Glu Leu Gln Ala Lys
        435                 440                 445
Leu Glu Ala Glu Ala Lys Ala Leu Lys Glu Gln Leu Ala Lys Gln Ala
    450                 455                 460
Glu Glu Leu Ala Lys Leu Arg Ala Gly Lys Ala Ser Asp Ser Gln Thr
465                 470                 475                 480
Pro Asp Ala Lys Pro Gly Asn Lys Val Val Pro Gly Thr Gly Gln Ala
                485                 490                 495
Pro Gln Ala Gly Thr Lys Pro Asn Gln Asn Lys Ala Pro Met Lys Glu
            500                 505                 510
Thr Lys Arg Gln Leu Pro Ser Thr Gly Glu Ala Ala Asn Pro Phe Phe
        515                 520                 525
Thr Ala Ala Ala Leu Thr Val Met Ala Thr Ala Gly Val Ala Ala Val
    530                 535                 540
Val Lys Arg Lys Glu Glu Asn Glu Ala Glu Phe Cys Arg Tyr Pro Ser
545                 550                 555                 560
His Trp Arg Pro Arg Leu
                565
```

```
<210> SEQ ID NO 15
<211> LENGTH: 1856
<212> TYPE: RNA
<213> ORGANISM: Artificial Sequence
<220> FEATURE:
<223> OTHER INFORMATION: Synthetic

<400> SEQUENCE: 15
gaagcuucuu guucuuuuug cagaagcuca gaauaaacgc ucaacuuugg cgagcucaua        60
gccauggcua aaauaccac gaauagacac uauucgcuua gaaauuaaa aacaggaacg         120 gcuucaguag caguagcuuu gacuguuuua gggacaggac ugguagcagg cagacagua        180 aaagcaagcc aaacagaacc aucucagacc aauaacagau uauaucaaga aagacaacgu       240
uuacaggauu uaaaaaguaa guuucaagac cugaaaaauc guucagaggg auacauucag       300
caauacuacg acgaagaaaa gaacaguggg aguaacucua acugguacgc aaccuacuua       360
```

| | |
|---|---|
| aaagaauuaa ugaacgaauu ugaacaagcu uauaaugaac uuagugguga ugguguaaaa | 420 |
| aaauuagcug caaguuugau ggaagaaaga gucgcuuuaa gagacgaaau cgaucagauu | 480 |
| aagaaaauau cagaagaauu aaaaaauaag cugagagcaa aagaagaaga auuaaaaaau | 540 |
| aaaaaagagg aacgugagcu ugagcaugcu gccuaugcag cagaugcaaa gaaacaugaa | 600 |
| gaauauguca aauccauguc ucucguacua auggauaaag aagaggagcg ucauaaacua | 660 |
| gagcaaucau uagacacggc uaaagcgag cuuguuaaaa aagagcaaga guucaguua | 720 |
| gucaaaggca aucuagauca aaaagaaaaa gaacuagaaa augaagagcu agcgaaagaa | 780 |
| agugcuauua gugauuugac ugagcagauu acugcuaaga aggcugaagu agaaaaauua | 840 |
| acucaagauu uagcugcuaa gucugcugaa auucaggaaa aagaagcuga aaaagaucgc | 900 |
| caacagcaua uguacgaagc guuuaugagc caguacaaag aaaaaguuga gaaacaagag | 960 |
| caagagcuug cuaagcuaaa acaacuugaa accaucaaca acaaucuauu agguaaugcu | 1020 |
| aaggauauga uagcuaaguu gucugcugaa aaugaacaau uagcaagcga caaagcaaaa | 1080 |
| cuugaagaac aaaacaagau uucagaagcg agccguaaag gucuucgucg ugacuuggac | 1140 |
| gcaucacgug aagcuaagaa acaaguugaa aaagauuuag caaacuugac ugcugaacuu | 1200 |
| gauaagguua aagaagauaa acaaauuuca gacgcaagcc guaaaggucu ucgucgugac | 1260 |
| uuggacgcau cacgugaagc uaagaaacaa guugaaaaag cuuuagaaga agcaaacagc | 1320 |
| aaauuagcgg cucuugaaaa acuuaacaaa gagcuugaag aaagcaagaa auuaacagaa | 1380 |
| aaagaaaaag cugagcuaca agcgaaacuu gaagcagaag caaaagcacu caagaacaa | 1440 |
| uuagcgaaac aagcugaaga acuugcaaaa cuaagagcug aaaagcauc agacucacaa | 1500 |
| accccugaug caaaaccagg aaacaaaguu guuccaggua caggucaagc accacaagca | 1560 |
| ggcacaaaac cuaaccaaaa caaagcacca augaaggaaa cuaagagaca guuaccauca | 1620 |
| acaggugaag cagcuaaucc auucuuuaca gcggcagccc uuacuguuau ggcaacagcu | 1680 |
| ggaguagcag caguuguaaa acgcaaagaa gaaaacgaag cugaauucug cagauaucca | 1740 |
| ucacacuggc ggccgcgacu cuaguaauga acuagucuuu uugaugccau ugccgacgcc | 1800 |
| cuuggcaagg guuaccacua aaccagccuc aagaacaccc gaauggaguc ggaucc | 1856 |

<210> SEQ ID NO 16
<211> LENGTH: 1720
<212> TYPE: RNA
<213> ORGANISM: Artificial Sequence
<220> FEATURE:
<223> OTHER INFORMATION: Synthetic

<400> SEQUENCE: 16

| | |
|---|---|
| gauagccaug gcuaaaaaua ccacgaauag acacuauucg cuuagaaaau uaaaaacagg | 60 |
| aacggcuuca guagcaguag cuuugacugu uuuagggaca ggacugguag cagggcagac | 120 |
| aguaaaagca agccaaacag aaccaucuca gaccaauaac agauuauauc aagaaagaca | 180 |
| acguuuacag gauuuaaaaa guaaguuuca agaccugaaa aaucguucag agggauacau | 240 |
| ucagcaauac uacgacgaag aaaagaacag uggaaguaac ucuaacuggu acgcaaccua | 300 |
| cuuaaaagaa uuaaaugacg aauuugaaca agcuuauaau gaacuuagug gugauggugu | 360 |
| aaaaaaauua gcugcaaguu ugauggaaga agagucgcu uuaagagacg aaaucgauca | 420 |
| gauuaagaaa auaucagaag aauuaaaaaa uaagcugaga gcaaaagaag aagaauuaaa | 480 |
| aaauaaaaaa gaggaacgug agcuugagca ugcugccuau gcagcagaug caaagaaaca | 540 |
| ugaagaauau gucaaaucca ugucucucgu acuaauggau aagaagagg agcgucauaa | 600 |

-continued

```
acuagagcaa ucauuagaca cggcuaaagc ugagcuuguu aaaaaagagc aagaguuaca      660
guuagucaaa ggcaaucuag aucaaaaaga aaaagaacua gaaaaugaag agcuagcgaa      720
agaaagugcu auuagugauu ugacugagca gauuacugcu aagaaggcug aaguagaaaa      780
auuaacucaa gauuuagcug cuaagucugc ugaaauucag gaaaaagaag cugaaaaaga      840
ucgccaacag cauauguacg aagcguuuau gagccaguac aaagaaaaag uugagaaaca      900
agagcaagag cuugcuaagc uaaaacaacu ugaaaccauc aacaacaauc uauuagguaa      960
ugcuaaggau augauagcua aguugucugc ugaaaaugaa caauuagcaa gcgacaaagc     1020
aaaacuugaa gaacaaaaca agauuucaga agcgagccgu aaaggucuuc gucgugacuu     1080
ggacgcauca cgugaagcua agaaacaagu ugaaaaagau uuagcaaacu ugacugcuga     1140
acuugauaag guuaaagaag auaaacaaau uucagacgca agccguaaag gucuucgucg     1200
ugacuuggac gcaucacgug aagcuaagaa acaaguugaa aaagcuuuag aagaagcaaa     1260
cagcaaauua gcggcucuug aaaaacuuaa caaagagcuu gaagaaagca agaaauuaac     1320
agaaaaagaa aaagcugagc uacaagcgaa acuugaagca gaagcaaaag cacucaaaga     1380
acaauuagcg aaacaagcug aagaacuugc aaaacuaaga gcuggaaaag caucagacuc     1440
acaaaccccu gaugcaaaac caggaaacaa aguuguucca gguacagguc aagcaccaca     1500
agcaggcaca aaaccuaacc aaaacaaagc accaaugaag gaaacuaaga gacaguuacc     1560
aucaacaggu gaagcagcua auccauucuu uacagcggca gcccuuacug uuauggcaac     1620
agcuggagua gcagcaguug uaaaacgcaa agaagaaaac gaagcugaau ucugcagaua     1680
uccaucacac uggcggccgc gacucuagua augacucgag                           1720
```

UNITED STATES PATENT AND TRADEMARK OFFICE
CERTIFICATE OF CORRECTION

PATENT NO. : 10,682,401 B2  
APPLICATION NO. : 15/583599  
DATED : June 16, 2020  
INVENTOR(S) : Michael J. P. Lawman et al.

Page 1 of 1

It is certified that error appears in the above-identified patent and that said Letters Patent is hereby corrected as shown below:

In the Specification

Column 29,  
Line 40, "CGGATCCGAATTCTCTAGA" should read --CGGATCCGAATTCTCTAGA--.

Column 30,  
Line 42, "CAGAAAAAGAAAAAGCUGAGCUACAAGCGAACUUGAAGCAGAAGCAAAAG" should read --CAGAAAAAGAAAAAGCUGAGCUACAAGCGAAACUUGAAGCAGAAGCAAAAG--.

Signed and Sealed this  
Sixth Day of October, 2020

Andrei Iancu  
*Director of the United States Patent and Trademark Office*